(12) United States Patent
Yoshino et al.

(10) Patent No.: US 9,485,405 B2
(45) Date of Patent: Nov. 1, 2016

(54) FOCUS CONTROL DEVICE, ENDOSCOPE DEVICE, AND FOCUS CONTROL METHOD

(71) Applicant: OLYMPUS CORPORATION, Shibuya-ku, Tokyo (JP)

(72) Inventors: Koichiro Yoshino, Tokyo (JP); Keiji Higuchi, Kunitachi (JP)

(73) Assignee: OLYMPUS CORPORATION, Tokyo (JP)

( * ) Notice: Subject to any disclaimer, the term of this patent is extended or adjusted under 35 U.S.C. 154(b) by 296 days.

(21) Appl. No.: 14/145,184

(22) Filed: Dec. 31, 2013

(65) Prior Publication Data
US 2014/0111628 A1    Apr. 24, 2014

Related U.S. Application Data

(63) Continuation of application No. PCT/JP2012/064097, filed on May 31, 2012.

(30) Foreign Application Priority Data

Aug. 23, 2011   (JP) ................................ 2011-181585
Feb. 15, 2012   (JP) ................................ 2012-030545

(51) Int. Cl.
*G03B 13/36*        (2006.01)
*H04N 5/232*        (2006.01)
(Continued)

(52) U.S. Cl.
CPC ....... *H04N 5/23212* (2013.01); *A61B 1/00188* (2013.01); *A61B 1/05* (2013.01);
(Continued)

(58) Field of Classification Search
CPC   A61B 1/00188; A61B 1/05; G02B 23/2438; G02B 23/2469; G02B 7/102; G03B 13/36; H04N 2005/2255; H04N 5/23212; H04N 5/23296; H04N 7/183

USPC .......................................................... 348/65
See application file for complete search history.

(56) References Cited

U.S. PATENT DOCUMENTS 3,941,121 A *  3/1976  Olinger et al. ............... 600/167
6,559,888 B1   5/2003  Doron
(Continued)

FOREIGN PATENT DOCUMENTS

CN          101369044 A    2/2009
EP           948198 A2    10/1999
(Continued)

OTHER PUBLICATIONS

Chinese Office Action (and English translation thereof) dated Sep. 29, 2015, issued in counterpart Chinese Application No. 201280040943.6.
(Continued)

*Primary Examiner* — Shan Elahi
(74) *Attorney, Agent, or Firm* — Holtz, Holtz & Volek PC

(57) ABSTRACT

A focus control device in an endoscope system, implements an autofocus operation in an appropriate state by setting a focus mode of an imaging optical system. The focus control device includes a focus control section that controls a focus of an imaging optical system that includes at least a zoom lens that adjusts an optical magnification, and sets a focus mode of the imaging optical system, and an image acquisition section that acquires an image through the imaging optical system, the focus mode including a fixed focus mode and an autofocus (AF) mode, and the focus control section switching the focus mode between the fixed focus mode and the AF mode corresponding to whether the zoom lens is positioned on a wide-angle side or a telescopic side relative to a reference point that is situated between a wide-angle end and a telescopic end.

25 Claims, 16 Drawing Sheets

(51) Int. Cl.
*A61B 1/00* (2006.01)
*G02B 23/24* (2006.01)
*H04N 7/18* (2006.01)
*A61B 1/05* (2006.01)
*G02B 7/10* (2006.01)
*H04N 5/225* (2006.01)

(52) U.S. Cl.
CPC ......... *G02B 7/102* (2013.01); *G02B 23/2438* (2013.01); *G02B 23/2469* (2013.01); *G03B 13/36* (2013.01); *H04N 5/23296* (2013.01); *H04N 7/183* (2013.01); *H04N 2005/2255* (2013.01)

(56) References Cited

U.S. PATENT DOCUMENTS

| | | | |
|---|---|---|---|
| 6,563,543 | B1 | 5/2003 | Doron |
| 6,661,585 | B2 | 12/2003 | Okawara |
| 6,693,667 | B1 | 2/2004 | Doron |
| 6,829,008 | B1 | 12/2004 | Kondo et al. |
| 7,719,602 | B2 | 5/2010 | Aoyama et al. |
| 7,995,132 | B2 | 8/2011 | Miyata et al. |
| 2003/0076410 | A1* | 4/2003 | Beutter .................. H04N 7/183 348/65 |
| 2004/0090546 | A1 | 5/2004 | Doron |
| 2005/0041136 | A1 | 2/2005 | Miyata et al. |
| 2005/0104992 | A1 | 5/2005 | Aoyama et al. |
| 2007/0055104 | A1* | 3/2007 | Kumei et al. ................ 600/176 |
| 2008/0021271 | A1* | 1/2008 | Pasero ............... A61B 1/00039 600/109 |
| 2009/0102962 | A1 | 4/2009 | Miyata et al. |
| 2009/0231482 | A1 | 9/2009 | Shikata |
| 2010/0210937 | A1* | 8/2010 | Tearney ............... A61B 5/0066 600/424 |
| 2011/0184236 | A1* | 7/2011 | Yoshino ...................... 600/109 |

FOREIGN PATENT DOCUMENTS

| | | |
|---|---|---|
| JP | 05045575 A | 2/1993 |
| JP | 8-106060 A | 4/1996 |
| JP | 2000-056213 A | 2/2000 |
| JP | 2000-156823 A | 6/2000 |
| JP | 2000-231055 A | 8/2000 |
| JP | 2002-253488 A | 9/2002 |
| JP | 2002-258164 A | 9/2002 |
| JP | 2003-101853 A | 4/2003 |
| JP | 2005070738 A | 3/2005 |
| JP | 2005148346 A | 6/2005 |
| JP | 2009-223056 A | 10/2009 |

OTHER PUBLICATIONS

International Search Report (ISR) dated Aug. 7, 2012 (and English translation thereof) in International Application No. PCT/JP2012/064097.

Japanese Office Action (and English translation thereof) dated Feb. 2, 2016, issued in counterpart Japanese Application No. 2012-030545.

* cited by examiner

FIG. 17

| POSITION OF MOVABLE LENS | RATIO OF MOVING AMOUNT OF MOVABLE LENS TO MOVING AMOUNT OF IMAGE POSITION |
|---|---|
| x1 | R1 |
| x2 | R2 |
| x3 | R3 |
| ⋮ | ⋮ |

FIG. 18

| POSITION OF MOVABLE LENS | RATIO OF MOVING AMOUNT OF MOVABLE LENS TO MOVING AMOUNT OF IMAGE POSITION | DISTANCE BETWEEN IMAGE PLANE AND EXIT PUPIL POSITION | DISTANCE BETWEEN CENTERS OF GRAVITY OF PUPILS |
|---|---|---|---|
| x1 | R1 | F1 | G1 |
| x2 | R2 | F2 | G2 |
| x3 | R3 | F3 | G3 |
| ⋮ | ⋮ | ⋮ | ⋮ |

FOCUS CONTROL DEVICE, ENDOSCOPE DEVICE, AND FOCUS CONTROL METHOD

CROSS REFERENCE TO RELATED APPLICATION

This application is a continuation of International Patent Application No. PCT/JP2012/064097, having an international filing date of May 31, 2012, which designated the United States, the entirety of which is incorporated herein by reference. Japanese Patent Application No. 2011-181585 filed on Aug. 23, 2011 and Japanese Patent Application No. 2012-030545 filed on Feb. 15, 2012 are also incorporated herein by reference in their entirety.

BACKGROUND

The present invention relates to a focus control device, an endoscope system, a focus control method, and the like.

An endoscope system having a zoom function has been put to practical use, and configured so that the entire digestive tract (object) is observed on the wide-angle (WIDE) side (normal observation), and part of the digestive tract is observed in a zoom state on the telescopic (TELE) side (zoom observation) by adjusting the angle of view and the optical magnification of the objective lens using the zoom lens.

The endoscope system having a zoom function is normally configured to implement the optical magnification necessary for zoom observation through the lens design so that the angle of view of the objective lens becomes narrow (i.e., the optical magnification increases) and the best object distance decreases on the TELE side. The term "best object distance" used herein refers to the distance from the end of the objective lens to the object when the image position of the object coincides with the image plane of the image sensor. Since the object can be more closely observed by decreasing the best object distance on the TELE side, the optical magnification during zoom observation can be increased.

On the other hand, since the moving amount of the image position due to the movement of the object position increases as the best object distance decreases, the depth of field normally becomes shallow. In recent years, the depth of field of an endoscope system having a zoom function may be 1 mm or less on the TELE side, and it may be difficult for the user to bring the object into focus. JP-A-2002-258164, JP-A-8-106060 and JP-A-2002-253488 propose an endoscope system having an autofocus (AF) function in order to solve the above problem, for example. In JP-A-2002-258164, the AF operation is performed during normal observation and zoom observation, for example.

SUMMARY

According to one aspect of the invention, there is provided a focus control device comprising:

a focus control section that controls a focus of an imaging optical system, and sets a focus mode of the imaging optical system, the imaging optical system including at least a zoom lens that adjusts an optical magnification; and an image acquisition section that acquires an image through the imaging optical system, the focus mode including a fixed focus mode and an autofocus (AF) mode, the focus control section switching the focus mode between the fixed focus mode and the AF mode corresponding to whether the zoom lens is positioned on a wide-angle side or a telescopic side relative to a reference point that is situated between a wide-angle end and a telescopic end, and the focus control section controlling the focus so that an in-focus object distance monotonously decreases when a position of the zoom lens has moved from the wide-angle side to the telescopic side in a state in which the fixed focus mode is selected as the focus mode.

According to another aspect of the invention, there is provided an endoscope system comprising:

an imaging optical system that includes at least a zoom lens that adjusts an optical magnification;

an image sensor that generates an image that corresponds to an object image formed by the imaging optical system; and a focus control section that controls a focus of the imaging optical system, and sets a focus mode of the imaging optical system, the focus mode including a fixed focus mode and an autofocus (AF) mode, and the focus control section switching the focus mode between the fixed focus mode and the AF mode corresponding to whether the zoom lens is positioned on a wide-angle side or a telescopic side relative to a reference point that is situated between a wide-angle end and a telescopic end.

According to another aspect of the invention, there is provided a focus control method that controls a focus of an imaging optical system that includes at least a zoom lens that adjusts an optical magnification, a focus mode of the imaging optical system including a fixed focus mode and an autofocus (AF) mode, the method comprising:

switching the focus mode between the fixed focus mode and the AF mode corresponding to whether the zoom lens is positioned on a wide-angle side or a telescopic side relative to a reference point that is situated between a wide-angle end and a telescopic end; and controlling the focus of the imaging optical system based on the focus mode that has been set to the fixed focus mode or the AF mode.

BRIEF DESCRIPTION OF THE DRAWINGS

Brief Description of Drawings

Figure 1:
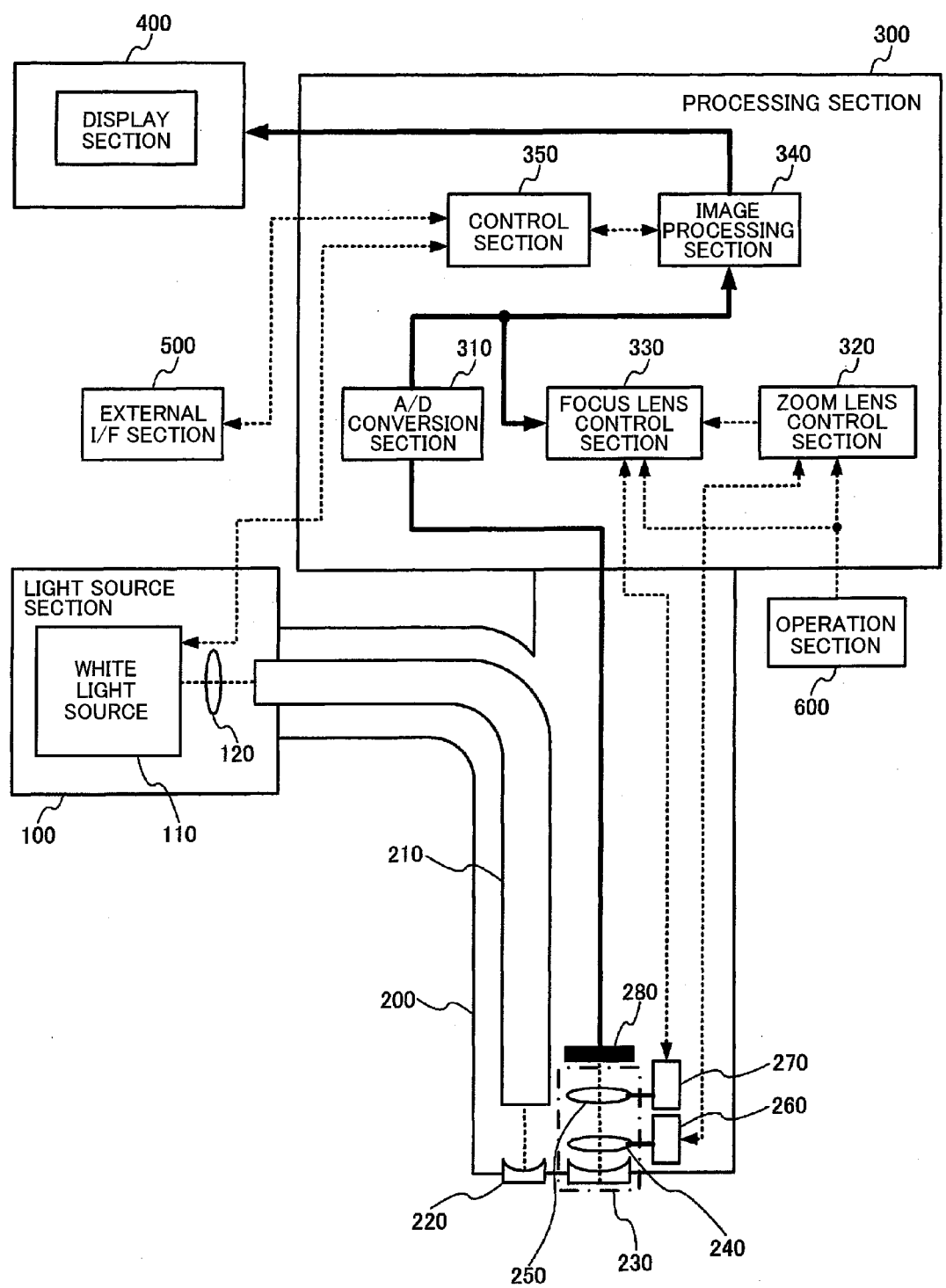

FIG. 1 illustrates a system configuration example of an endoscope system according to one embodiment of the invention.

Figure 2:
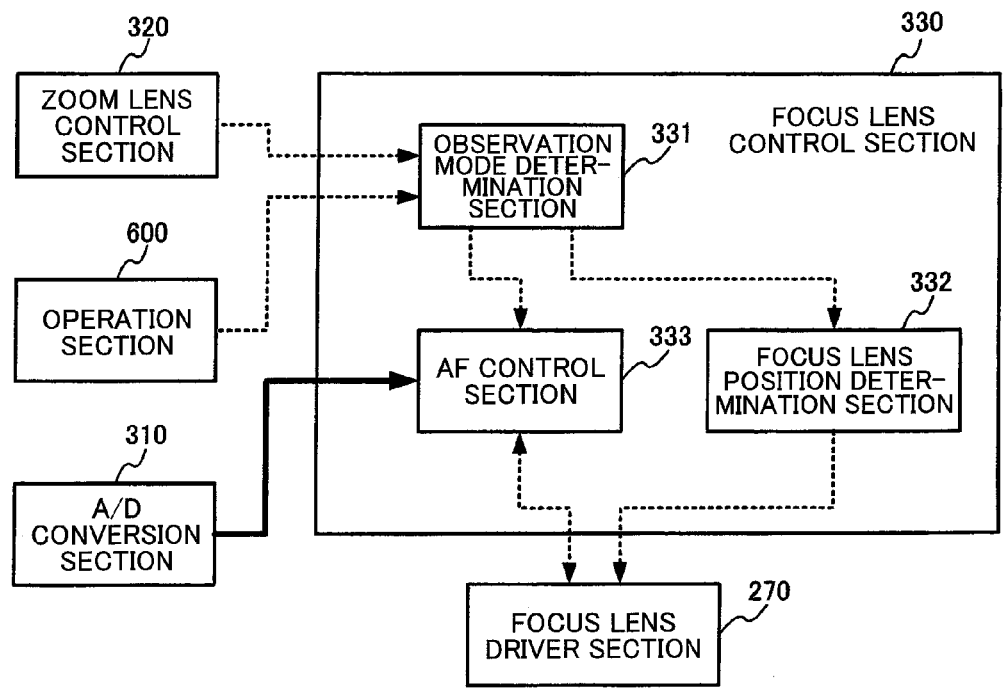

FIG. 2 illustrates a configuration example of a focus lens control section.

Figure 3:
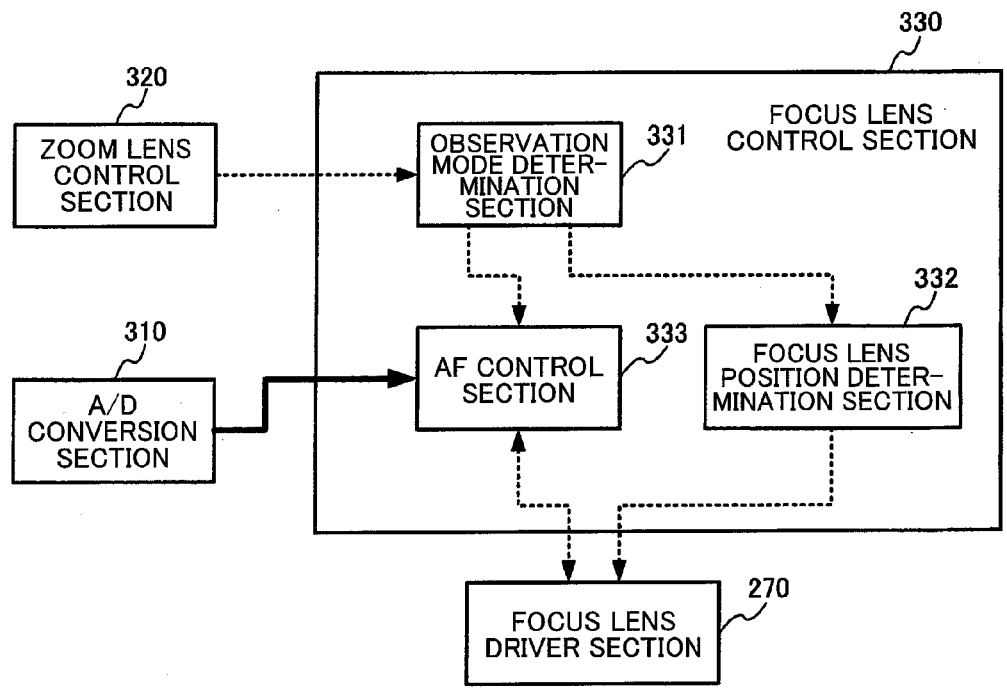

FIG. 3 illustrates another configuration example of a focus lens control section.

Figure 4A:
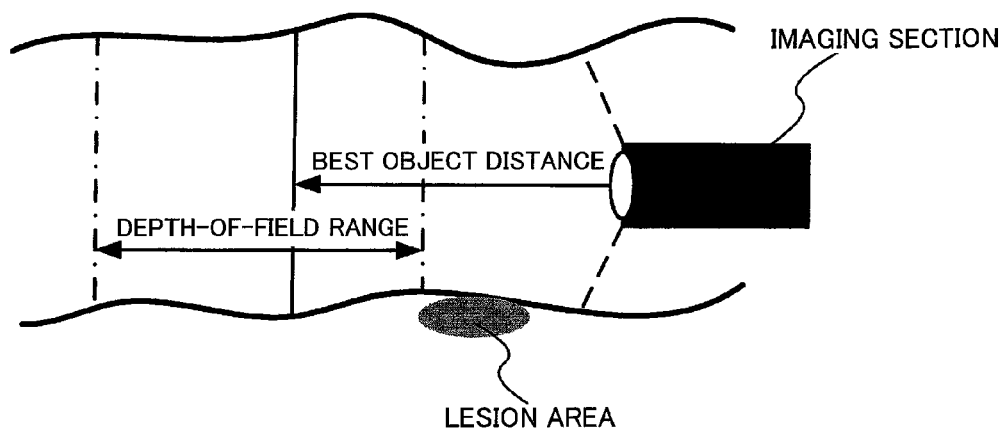
Figure 4B:
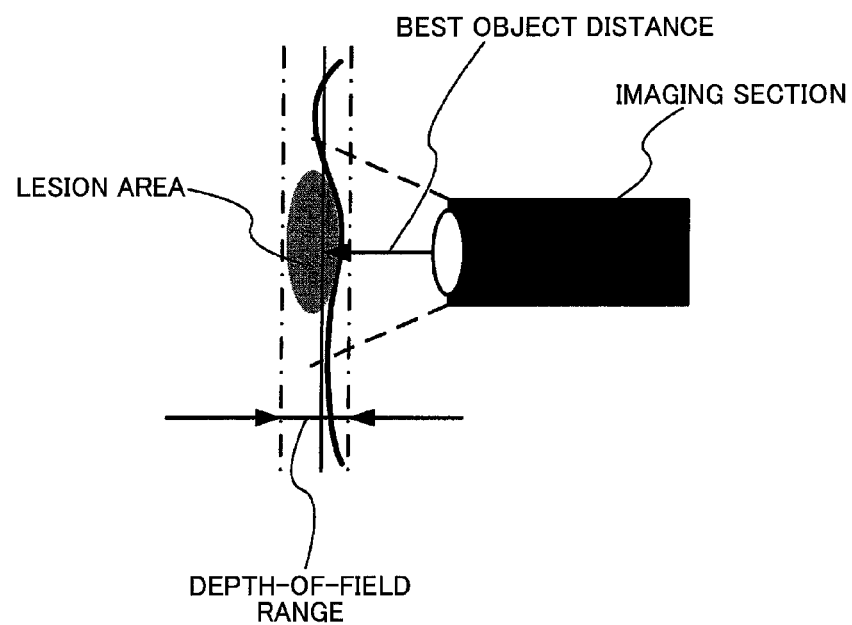

FIG. 4A is a view illustrating the relationship between an imaging section and an object when a zoom lens is positioned on a wide-angle side, and FIG. 4B is a view illustrating the relationship between an imaging section and an object when a zoom lens is positioned on a telescopic side.

Figure 5:
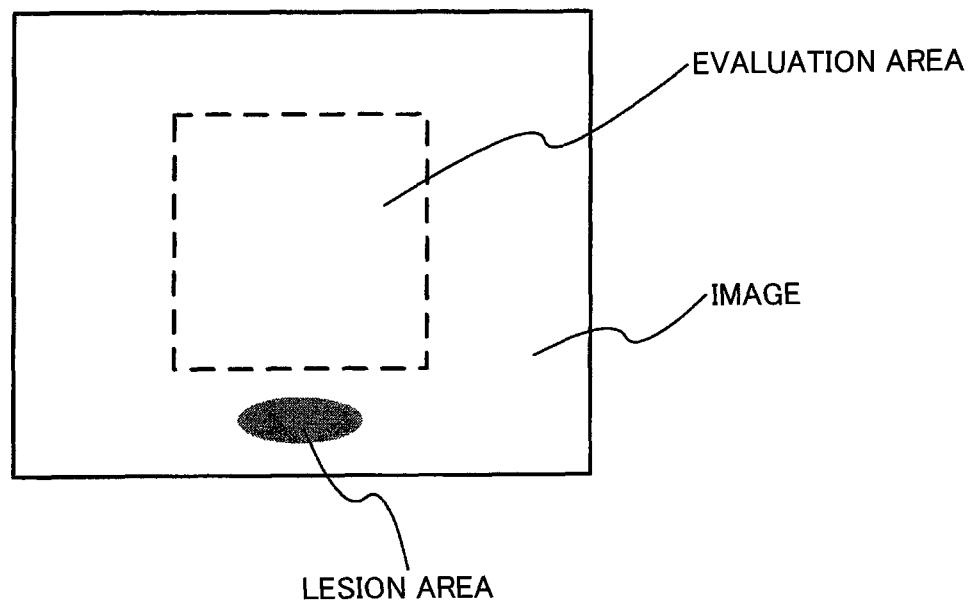

FIG. 5 is a view illustrating a situation in which an AF operation is not effective depending on an evaluation area setting.

Figure 6A:
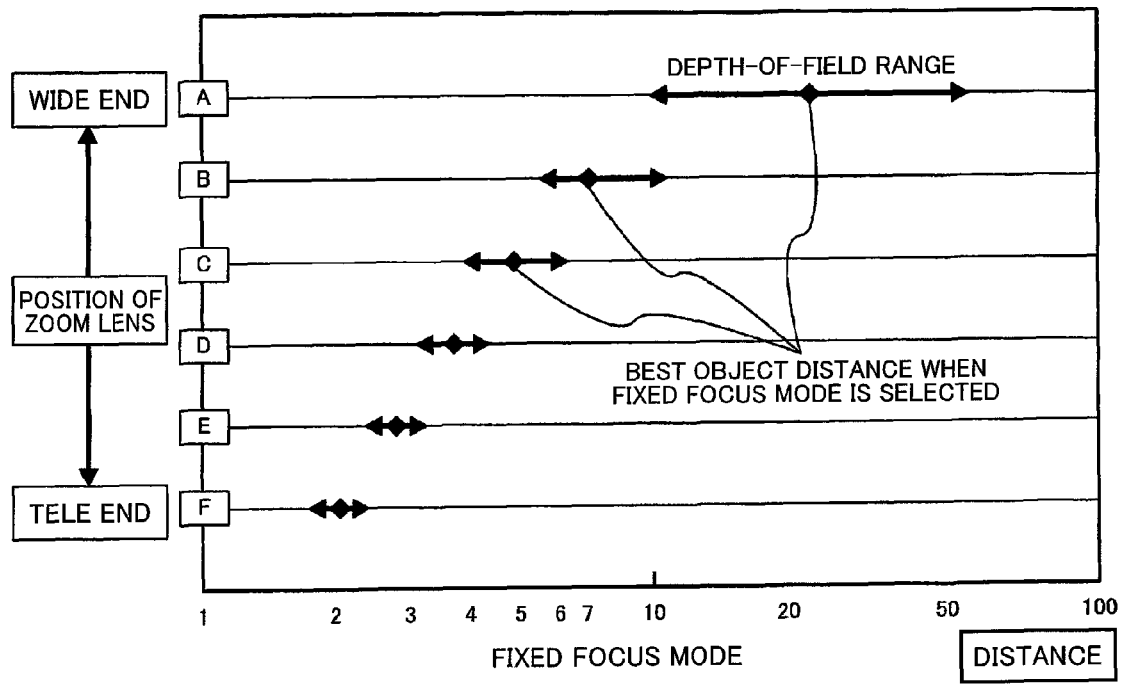
Figure 6B:
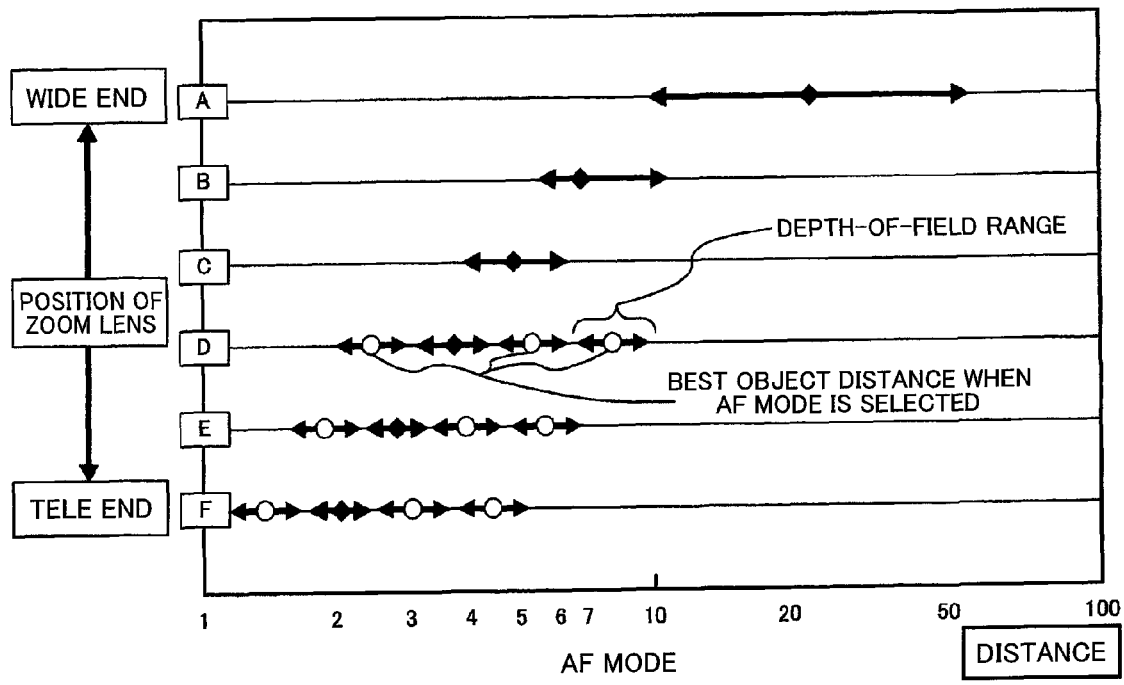

FIG. 6A is a view illustrating the relationship between the position of a zoom lens and a depth of field in a fixed focus mode, and FIG. 6B is a view illustrating the relationship between the position of a zoom lens and a depth of field in an AF mode.

Figure 7:
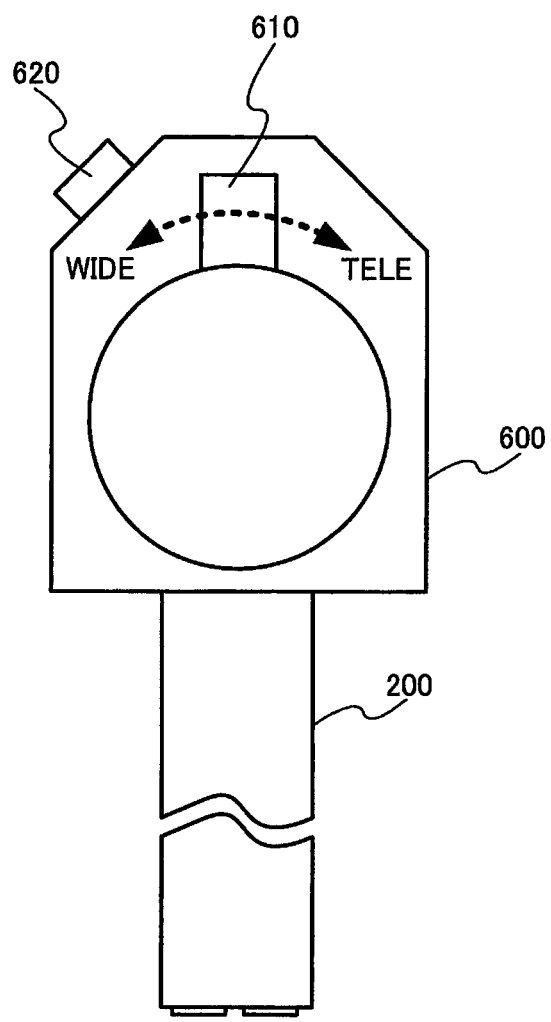

FIG. 7 illustrates a configuration example of an operation section.

Figure 8:
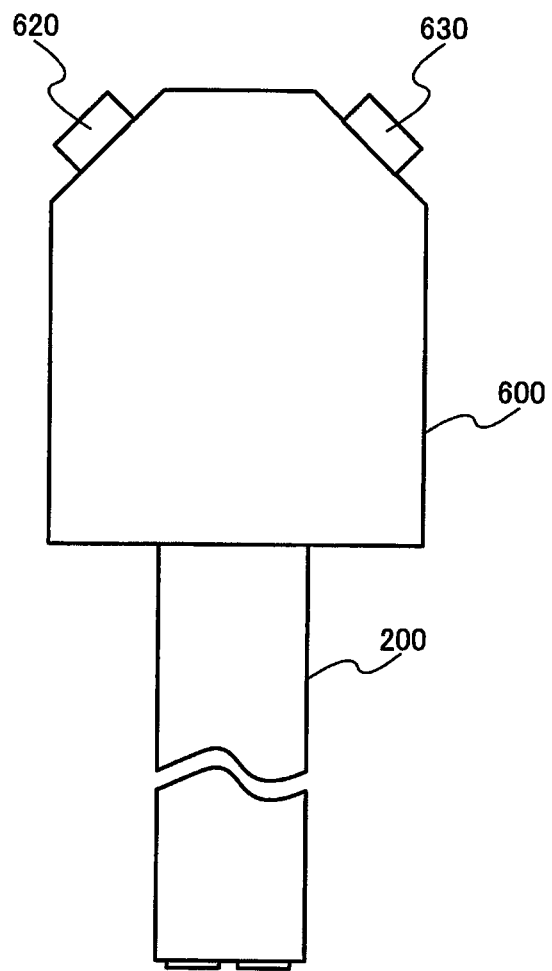

FIG. 8 illustrates another configuration example of an operation section.

Figure 9:
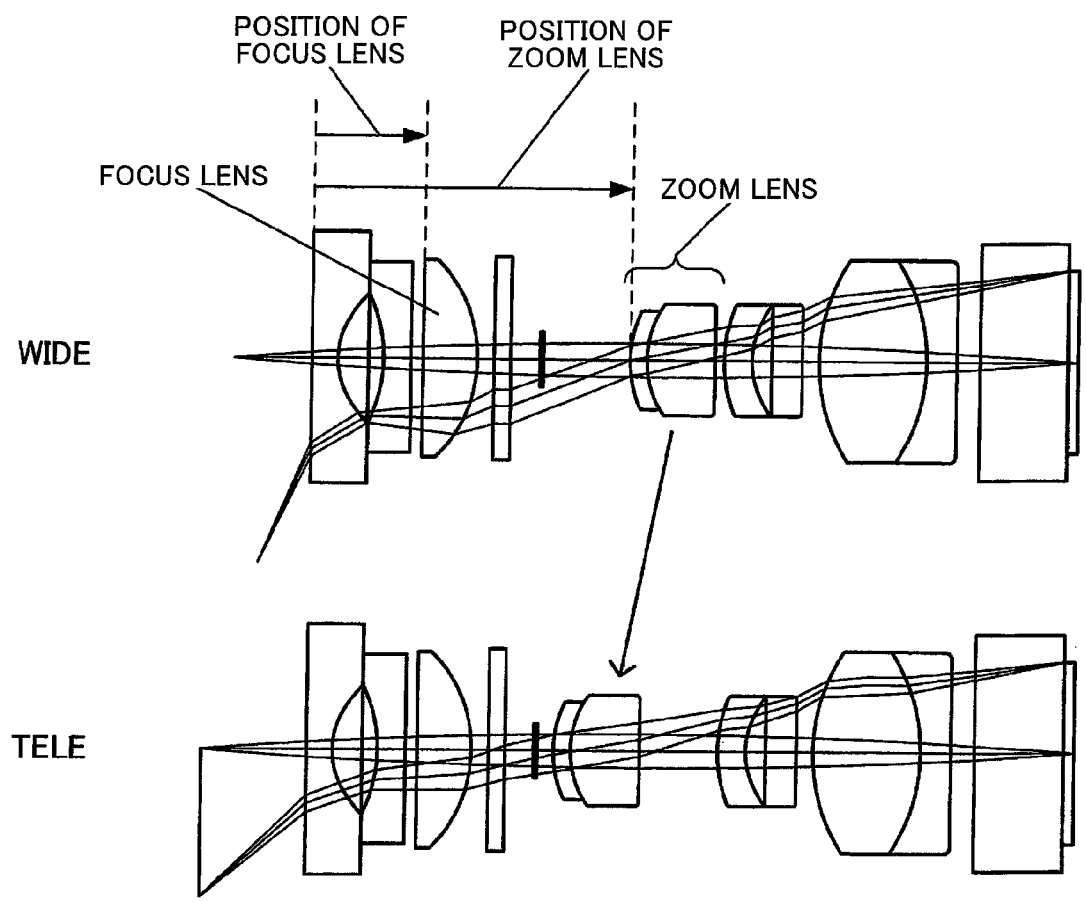

FIG. 9 illustrates a configuration example of an objective lens system (imaging optical system).

Figure 10:
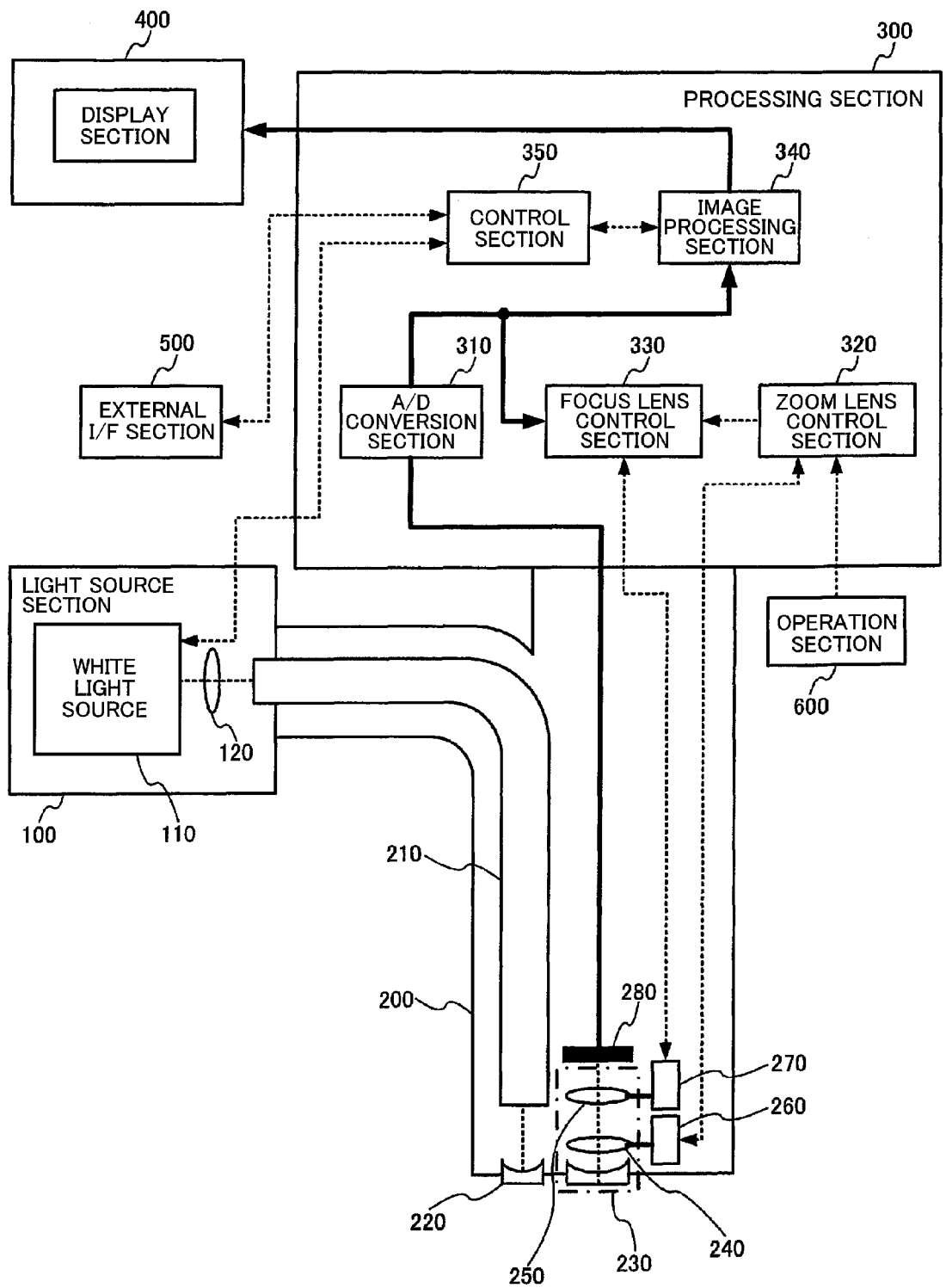

FIG. 10 illustrates another system configuration example of an endoscope system according to one embodiment of the invention.

Figure 11:
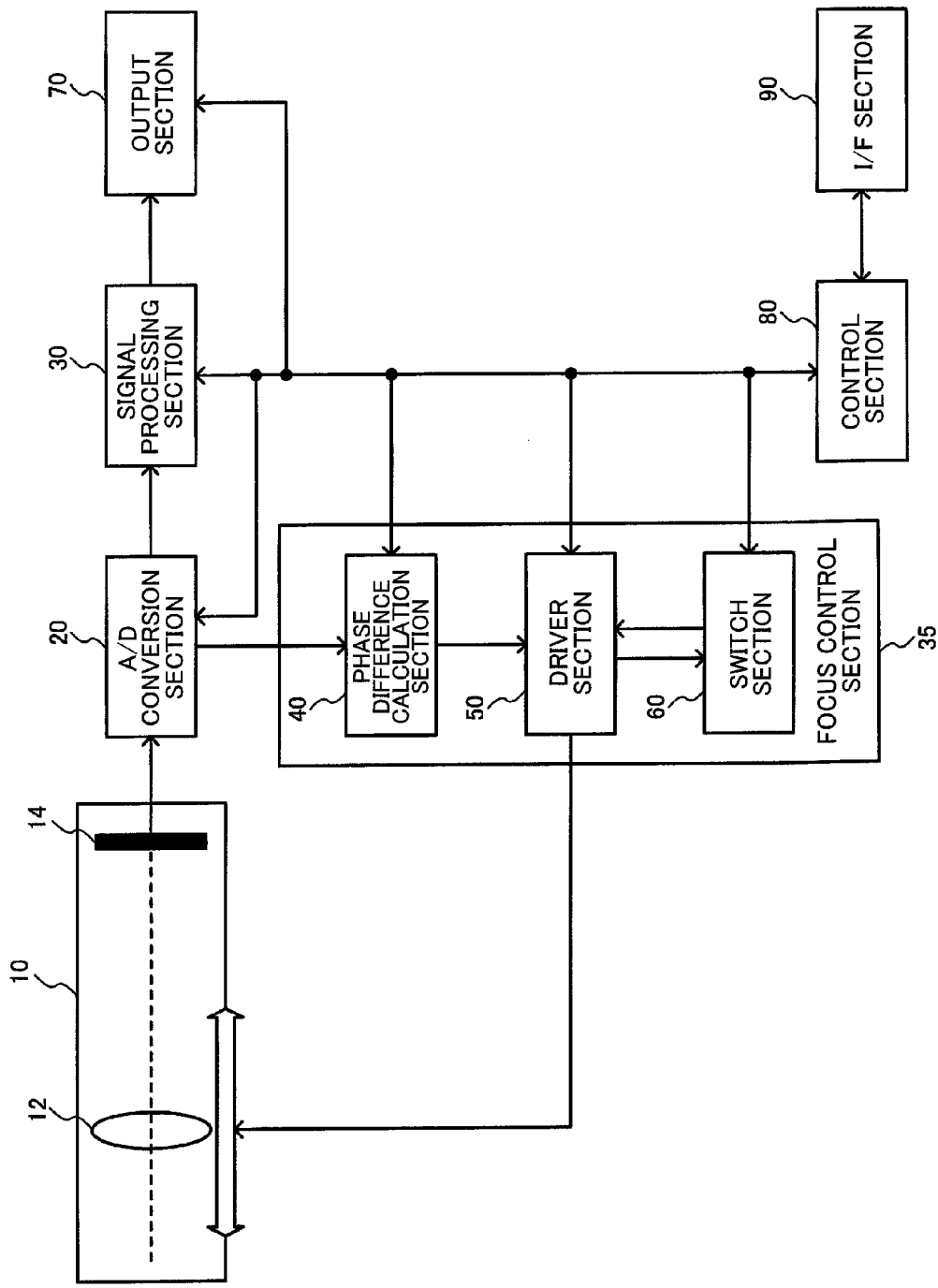

FIG. 11 illustrates a system configuration example of an endoscope system according to a fourth embodiment.

Figure 12:
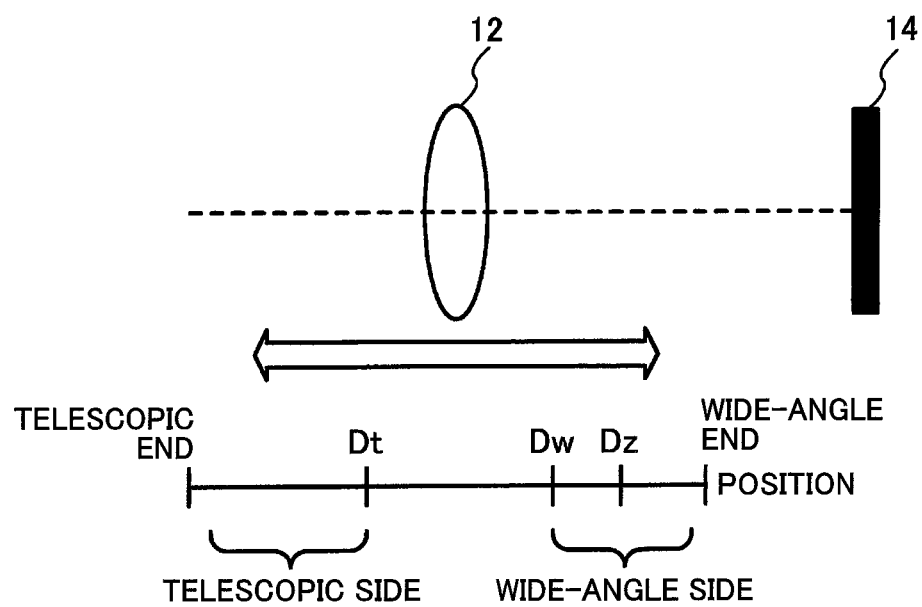

FIG. 12 is a view illustrating a mode switch control process.

Figure 13:
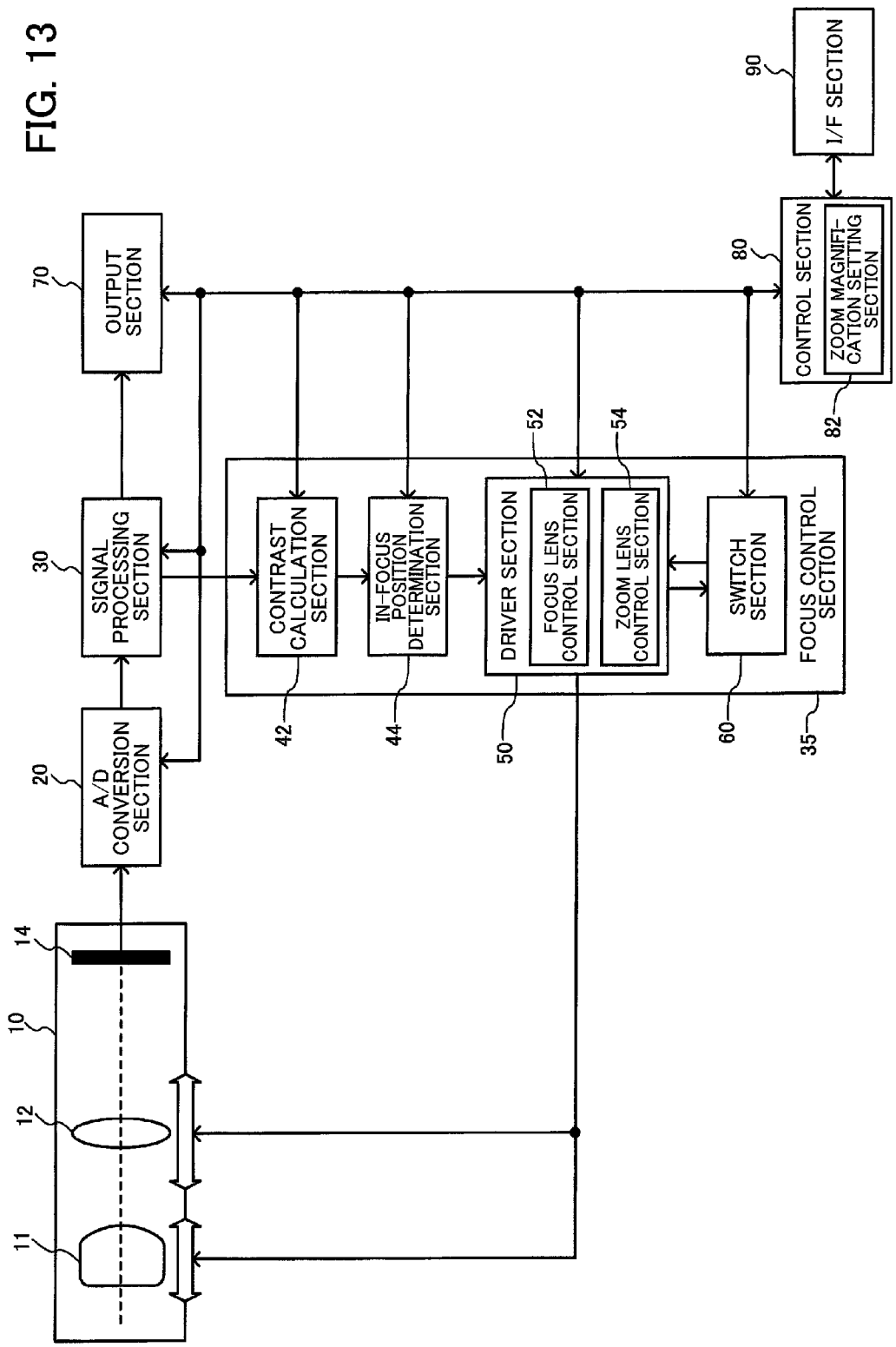

FIG. 13 illustrates a system configuration example of an endoscope system according to a fifth embodiment.

Figure 14:
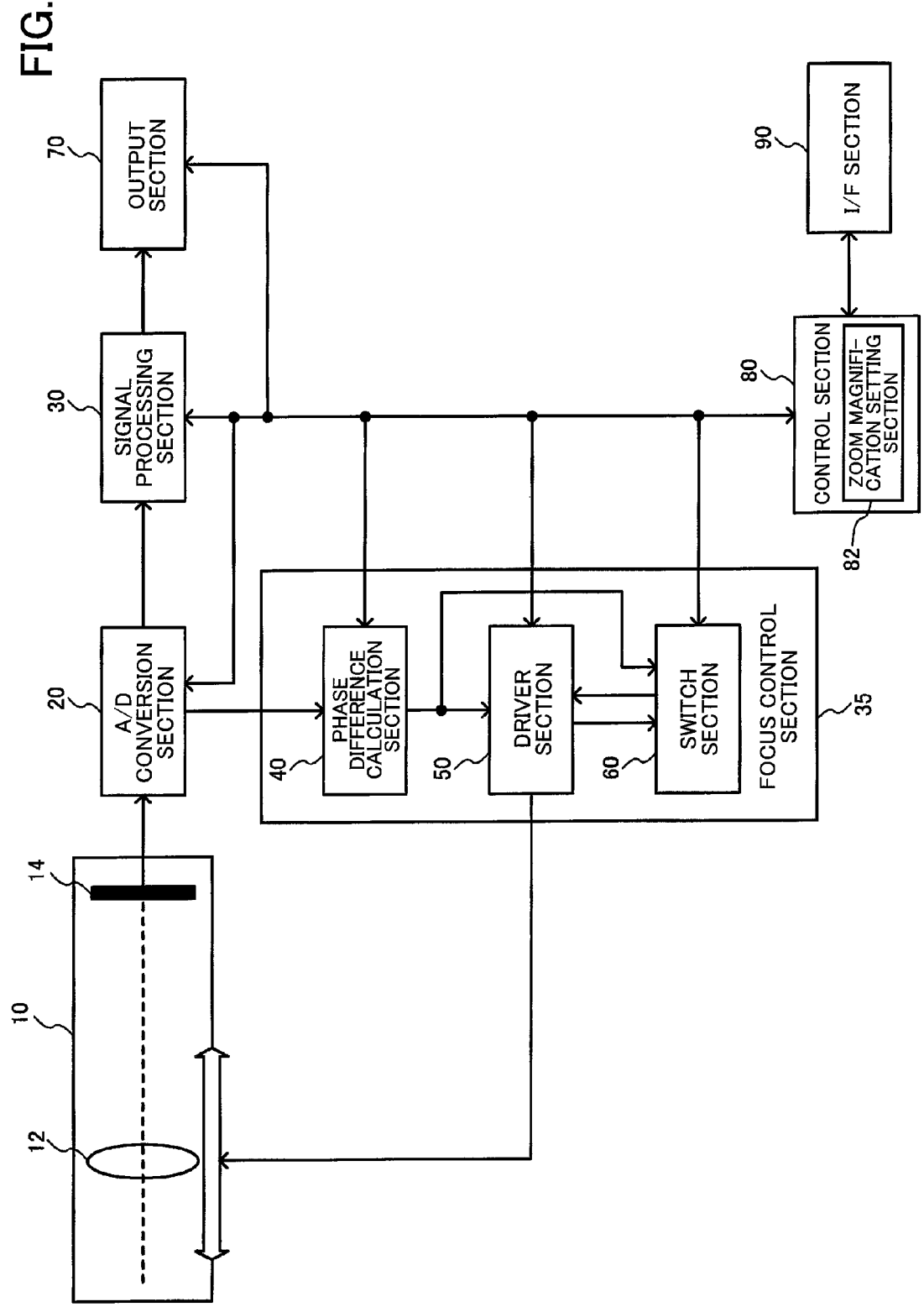

FIG. 14 illustrates a system configuration example of an endoscope system according to a sixth embodiment.

Figure 15:
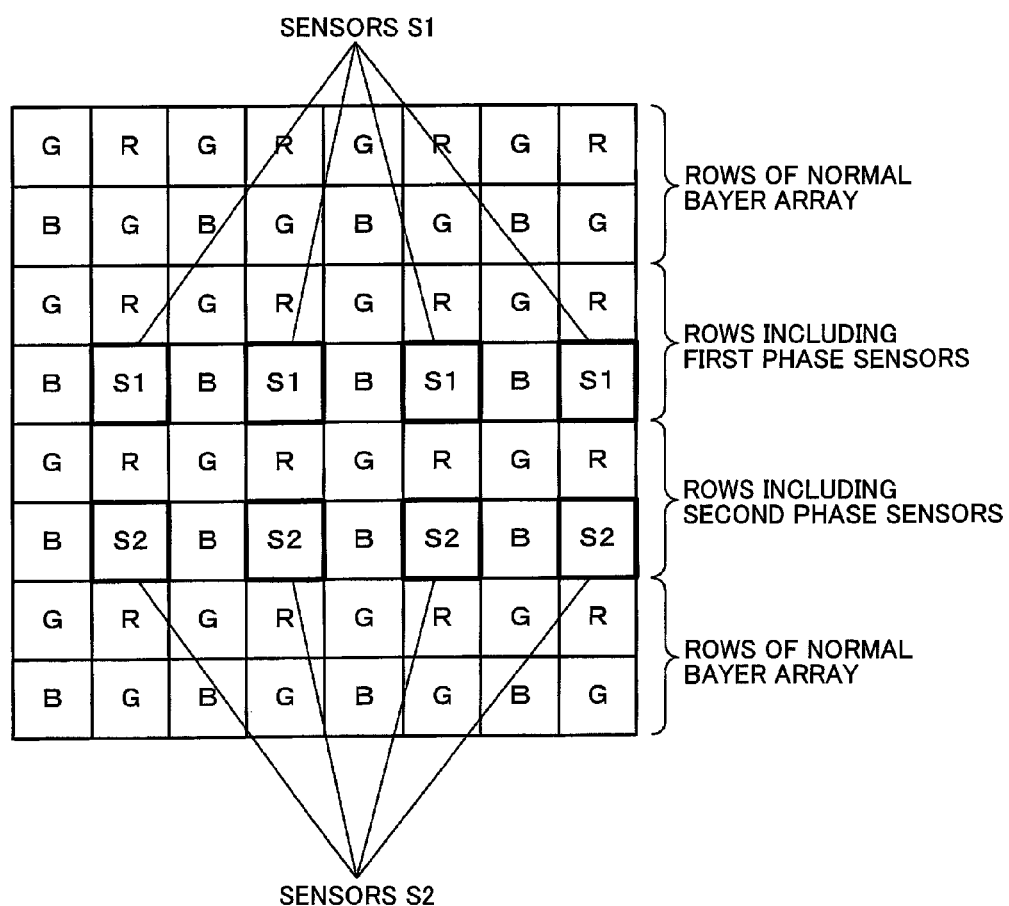

FIG. 15 illustrates a configuration example of an image sensor that includes a phase difference detection device.

Figure 16:
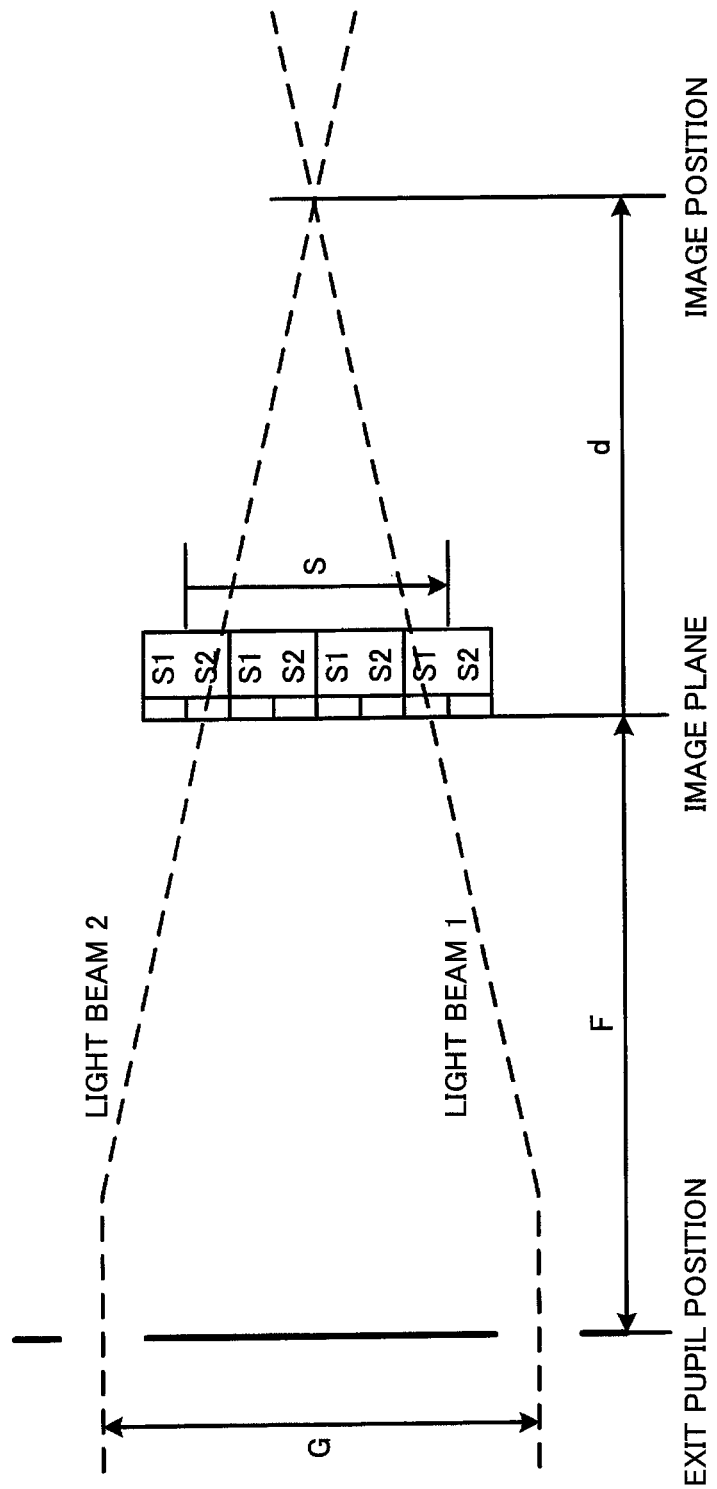

FIG. 16 is a view illustrating a phase detection AF operation.

FIG. 17 illustrates a first example of a look-up table used for a phase detection AF operation.

FIG. 18 illustrates a second example of a look-up table used for a phase detection AF operation.

DESCRIPTION OF EXEMPLARY EMBODIMENTS

According to one embodiment of the invention, there is provided a focus control device comprising:

a focus control section that controls a focus of an imaging optical system, and sets a focus mode of the imaging optical system, the imaging optical system including at least a zoom lens that adjusts an optical magnification; and an image acquisition section that acquires an image through the imaging optical system, the focus mode including a fixed focus mode and an autofocus (AF) mode, the focus control section switching the focus mode between the fixed focus mode and the AF mode corresponding to whether the zoom lens is positioned on a wide-angle side or a telescopic side relative to a reference point that is situated between a wide-angle end and a telescopic end, and the focus control section controlling the focus so that an in-focus object distance monotonously decreases when a position of the zoom lens has moved from the wide-angle side to the telescopic side in a state in which the fixed focus mode is selected as the focus mode.

According to another embodiment of the invention, there is provided an endoscope system comprising:

an imaging optical system that includes at least a zoom lens that adjusts an optical magnification;

an image sensor that generates an image that corresponds to an object image formed by the imaging optical system; and a focus control section that controls a focus of the imaging optical system, and sets a focus mode of the imaging optical system, the focus mode including a fixed focus mode and an autofocus (AF) mode, and the focus control section switching the focus mode between the fixed focus mode and the AF mode corresponding to whether the zoom lens is positioned on a wide-angle side or a telescopic side relative to a reference point that is situated between a wide-angle end and a telescopic end.

According to another embodiment of the invention, there is provided a focus control method that controls a focus of an imaging optical system that includes at least a zoom lens that adjusts an optical magnification, a focus mode of the imaging optical system including a fixed focus mode and an autofocus (AF) mode, the method comprising:

switching the focus mode between the fixed focus mode and the AF mode corresponding to whether the zoom lens is positioned on a wide-angle side or a telescopic side relative to a reference point that is situated between a wide-angle end and a telescopic end; and controlling the focus of the imaging optical system based on the focus mode that has been set to the fixed focus mode or the AF mode.

Exemplary embodiments of the invention are described below. Note that the following exemplary embodiments do not in any way limit the scope of the invention laid out in the claims. Note also that all of the elements described below in connection with the following exemplary embodiments should not necessarily be taken as essential elements of the invention.

1. First Embodiment

An endoscope system according to a first embodiment of the invention is described below with reference to FIG. 1. The endoscope system according to the first embodiment includes a light source section 100, an imaging section 200, a processing section 300, a display section 400, an external I/F section 500, and an operation section 600.

The light source section 100 includes a white light source 110 that emits white light, and a condenser lens 120 that focuses the white light on a light guide fiber 210.

The imaging section 200 is formed to be elongated and flexible (i.e., can be curved) so that the imaging section 200 can be inserted into a body cavity or the like. The imaging section 200 includes the light guide fiber 210 that guides the light focused by the light source section 100, an illumination lens 220 that diffuses the light guided by the light guide fiber 210, and applies the diffused light to an observation target, an objective lens system 230 that forms an image of the reflected light from the observation target, a zoom lens 240 that is included in the objective lens system 230, and adjusts the optical magnification, a focus lens 250 that is included in the objective lens system 230, and adjusts the focal distance, a zoom lens driver section 260 that drives the zoom lens 240, a focus lens driver section 270 that drives the focus lens 250, and an image sensor 280 that photoelectrically converts the reflected light to generate an image. The zoom lens driver section 260 and the focus lens driver section 270 are implemented by a voice coil motor (VCM), for example. The image sensor 280 is an image sensor that includes a Bayer color filter array, for example.

The processing section 300 includes an A/D conversion section 310, a zoom lens control section 320, a focus lens control section 330 (focus control section in a broad sense), an image processing section 340, and a control section 350. The A/D conversion section 310 converts analog signals output from the image sensor 280 into digital image signals, and outputs the digital image signals to the focus lens control section 330 and the image processing section 340.

The zoom lens control section 320 is connected to the operation section 600, the zoom lens driver section 260, and the focus lens control section 330, and controls the position of the zoom lens according to information output from the operation section 600. The zoom lens control section 320 outputs position information about the zoom lens to the focus lens control section 330. The focus lens control section 330 is connected to the operation section 600, the focus lens driver section 270, and the zoom lens control section 320, and controls the position of the focus lens according to information output from the operation section 600, and the position information about the zoom lens output from the zoom lens control section 320. Note that the position of the focus lens and the position of the zoom lens are respectively defined as the position of the front end of the focus lens and the position of the front end of the zoom lens with respect to the front end of the objective lens system 230. The details of the operation section 600, the zoom lens control section 320, and the focus lens control section 330 are described later.

The image processing section 340 performs image processing (e.g., white balance process, interpolation process (demosaicing process), color conversion process, grayscale transformation process, and noise reduction process) on the image signals output from the AD conversion section 310, and outputs the resulting image signals to the display section 400. The display section 400 is a liquid crystal monitor, for example. The display section 400 displays an image based on the image signals output from the image processing section 340. The control section 330 is bidirectionally connected to the white light source 110, the image processing section 340, and the external I/F section 500, and controls the white light source 110, the image processing section 340, and the external IN section 500 according to input information output from the external I/F section 500. The external I/F section 500 is an interface that allows the user to perform an input operation or the like on the endoscope system. The external I/F section 500 includes a start button for starting/stopping the imaging operation, an exposure adjustment button for adjusting the brightness of the image, an adjustment button for adjusting the imaging conditions and the image processing parameters, and the like.

The details of the operation section 600, the zoom lens control section 320, and the focus lens control section 330 are described below. FIG. 7 illustrates an example of the operation section 600 according to the first embodiment. The operation section 600 according to the first embodiment is integrated with the imaging section 200, for example. The operation section 600 includes a zoom lever 610 and an AF button 620. The zoom lever 610 can be continuously operated within a given range, for example. The user can continuously adjust the position of the zoom lens from the WIDE end to the TELE end by moving the zoom lever 610. Specifically, the operation section 600 outputs position information about the zoom lever 610 to the zoom lens control section 320, for example. The zoom lens control section 320 links the position information about the zoom lever 610 to the position information about the zoom lens using a look-up table set in advance or the like, and outputs the position information about the zoom lens to the zoom lens driver section 260. The zoom lens driver section 260 drives the zoom lens 240 based on the position information about the zoom lens output from the zoom lens control section 320. The zoom lens control section 320 also outputs the position information about the zoom lens to the focus lens control section 330. The operation section 600 alternately outputs an AF start/stop signal to the focus lens control section 330 each time the AF button 620 has been pressed, for example.

FIG. 2 illustrates an example of the focus lens control section 330 according to the first embodiment. The focus lens control section 330 (focus control section in a broad sense) includes an observation mode determination section 331, a focus lens position determination section 332, and an AF control section 333. The observation mode determination section 331 determines the observation mode (focus mode) based on the position information about the zoom lens output from the zoom lens control section 320, and AF start/stop information output from the operation section 600. Specifically, the observation mode determination section 331 selects a fixed focus mode when the zoom lens is positioned on the WIDE side relative to a given position D, and outputs the position information about the zoom lens to the focus lens position determination section 332. The observation mode determination section 331 also selects the fixed focus mode when the zoom lens is positioned on the TELE side relative to the given position D, and the AF start signal is not output from the operation section 600, and outputs the position information about the zoom lens to the focus lens position determination section 332. The focus lens position determination section 332 determines the position of the focus lens based on the position information about the zoom lens, and outputs position information about the focus lens to the focus lens driver section 270. The focus lens driver section 270 drives the focus lens 250 based on the position information about the focus lens output from the focus lens position determination section 332.

The observation mode determination section 331 selects an AF mode when the zoom lens is positioned on the TELE side relative to the given position D, and the AF start signal has been output from the operation section 600, and outputs an AF start signal to the AF control section 333. The observation mode determination section 331 outputs an AF stop signal to the AF control section 333 when the zoom lens is positioned on the TELE side relative to the given position D, and the AF stop signal has been output from the operation section 600. The AF control section 333 starts an AF operation according to the AF start signal output from the observation mode determination section 331. For example, the AF control section 333 calculates a contrast value from the image signals output from the A/D conversion section 310, and drives the focus lens based on a known contrast AF technique. The AF control section 333 may determine whether or not an in-focus state has occurred from the calculated contrast value, and stop the AF operation when it has been determined that the in-focus state has occurred. Alternatively, the AF control section 333 may drive the focus lens based on a known continuous AF technique so that the AF operation is continuously performed until the AF stop signal is output from the observation mode determination section 331. The image sensor 280 may include a sensor for acquiring phase difference information (not illustrated in the drawings), for example. In this case, the A/D conversion section 310 may generate digital phase difference information from the analog signals output from the image sensor 280, and output the phase difference information to the AF control section 333, and the AF control section 333 may drive the focus lens based on a known phase detection AF technique.

The details of the focus lens position determination method implemented by the lens position determination section 332 are described below. FIG. 6A is a view illustrating the position of the zoom lens, the corresponding best object distance, and the depth-of-field range when the fixed focus mode is selected. In the first embodiment, the position of the zoom lens can be continuously moved by operating the zoom lever 610. Note that FIG. 6A illustrates the case where the position of the zoom lens is moved stepwise for convenience of explanation. The focus lens position determination section 332 determines the position of the focus lens based on the position information about the zoom lens output from the observation mode determination section 331 so that the best object distance decreases as the position of the zoom lens is moved from the WIDE end to the TELE end (see FIG. 6A). When the position of the zoom lens and the best object distance that it is desired to implement at the position of the zoom lens have been determined, the position of the focus lens is uniquely calculated from the design data of the objective lens system 230. Therefore, the focus lens position determination section 332 may determine the position of the focus lens from the position of the zoom lens using a look-up table set in advance that links the position of the zoom lens to the position of the focus lens, for example.

FIG. 9 illustrates an example of the objective lens system 230 according to the first embodiment. The objective lens system 230 is designed so that the angle of view becomes narrow (i.e., the optical magnification increases) and the best object distance decreases when the focus lens is fixed at a given reference position, and the position of the zoom lens is moved from the WIDE end to the TELE end. When using such an objective lens system, the focus lens position determination section 332 can implement the best object distance and the depth-of-field range illustrated in FIG. 6A by always fixing the focus lens at the reference position independently of the position of the zoom lens. For example, the objective lens system of a digital camera is generally designed so that the best object distance is almost constant even when the angle of view is adjusted by adjusting the position of the zoom lens. When using such an objective lens system, the focus lens position determination section 332 can implement the best object distance and the depth-of-field range illustrated in FIG. 6A by adjusting the position of the focus lens so that the best object distance decreases as the position of the zoom lens is moved from the WIDE end to the TELE end.

An operation performed by the user when performing normal observation and zoom observation is described below with reference to FIGS. 6A and 6B. The user moves the zoom lever 610 to the WIDE end, and performs normal observation for finding a lesion area (position A in FIG. 6A). In this case, the imaging section 200 can acquire an image having a wide angle of view and a deep depth of field (see FIG. 4A). In this case, the depth-of-field range is about 10 to about 50 mm (see FIG. 6A).

When the user has found a lesion area, the user zooms in on the lesion area while moving the imaging section 200 closer to the lesion area. In the first embodiment, when the distance to the lesion area has decreased to 10 mm or less, the lesion area lies outside the depth of field, and becomes out of focus. In this case, the user moves the zoom lever 610 toward the TELE end to bring the depth-of-field range close to the imaging section (positions B and C in FIG. 6A). Therefore, the lesion area lies within the depth of field again, and the user can continue observation of the lesion area. Note that the user may cause the lesion area to lie within the depth of field by operating the zoom lever 610 while changing the position of the imaging section 200.

In the first embodiment, the depth-of-field range is about 4 to about 7 mm (i.e., a certain depth of field is maintained) even when the zoom lens has been moved to the position C. In such a case, the user normally observes the object in a state in which the imaging section 200 is parallel to (or tilted to some extent relative to) the wall surface of the digestive tract (i.e., object) (see FIG. 4A). In this case, the distance to the object differs to a large extent depending on the position of the object within the acquired image, as described above. Since it is difficult to determine the position of the lesion area (i.e., the observation target for the user) within the image from the acquired image, it is difficult to accurately bring the lesion area into focus using the AF operation. However, since a certain depth of field is maintained, the fixed focus mode is selected by the observation mode determination section 331, and the user can easily bring the lesion area into focus by operating the zoom lever 610 or adjusting the position of the imaging section 200.

The user then moves the zoom lever 610 toward the TELE end while moving the imaging section 200 closer to the lesion area to further zoom in on the lesion area. In the first embodiment, when the zoom lens is positioned on the TELE side relative to the position D, the depth of field when the fixed focus mode is selected is about 1 mm or less (see FIG. 6A). In such a case, the user normally observes the object in a state in which the imaging section 200 is almost orthogonal to the wall surface of the digestive tract (i.e., object) (see FIG. 4B). Specifically, when the depth of field is shallow, only a narrow area of the image is brought into focus if the imaging section 200 is not orthogonal to the object. In this case, it is difficult for the user to bring the object into focus by operating the zoom lever 610 or adjusting the position of the imaging section 200. Therefore, the user starts the AF operation by pressing the AF button 620. The AF mode is then selected by the observation mode determination section 331, and the position of the focus lens is controlled corresponding to the distance to the object (see FIG. 6B). Therefore, the user can easily bring the object into focus.

In the first embodiment, the AF operation is controlled to be performed within the range from the position D to the TELE end (position F). Note that the position D may be set to the TELE end when the optical magnification is sufficient for zoom observation when the best object distance is minimized by moving the position of the focus lens in a state in which the zoom lens is set to the position D, for example. In this case, the observation mode determination section 331 may select the AF mode when the zoom lens is positioned at the TELE end, and the AF start/stop signal has been output from the operation section 600, and output the AF start/stop signal to the AF control section 333.

According to the first embodiment, a focal distance control device (focus control device) includes the focus lens control section 330 that controls the position of the focus lens 250, and sets the focus mode of the imaging optical system, and an image acquisition section (corresponding to the A/D conversion section 310, for example) that acquires an image through the imaging optical system. The imaging optical system includes the zoom lens 240 that adjusts the optical magnification, and the focus lens 250 that adjusts the focal distance. The focus mode includes the fixed focus mode and the AF (autofocus) mode. The focus lens control section 330 switches the focus mode between the fixed focus mode and the AF mode corresponding to whether the zoom lens 240 is positioned on the wide-angle side or the telescopic side relative to a reference point, the reference point being set at a position between the wide-angle end and the telescopic end of the position of the zoom lens.

The term "fixed focus mode" used herein refers to a mode in which the focus lens 250 is set at a position that is determined corresponding to the position of the zoom lens 240 when the position of the zoom lens 240 has been determined. The fixed focus mode is the mode illustrated in FIG. 6A, for example. When the position of the zoom lens has been determined, the best object distance (in-focus object distance (details thereof are described later)) is uniquely determined. This means that the position of the focus lens is determined corresponding to the position of the zoom lens since the best object distance changes corresponding to the position of the focus lens 250.

The term "AF mode" used herein refers to a mode in which the autofocus operation is performed. The autofocus operation is implemented using a known autofocus method. For example, a contrast AF method or a phase detection AF method may be used. The AF mode is the mode illustrated in FIG. 6B, for example. In particular, the AF mode corresponds to the case where the position of the zoom lens is D to F. In the AF mode, the best object distance is not uniquely determined even when the position of the zoom lens has been determined (see FIG. 6B). For example, when using a contrast AF method, the best object distance is set so that an evaluation area (contrast value calculation target area) set within the acquired image is brought into focus. The best object distance is set by adjusting the position of the focus lens 250.

The term "focal distance" used herein refers to the position of the object relative to the end of the objective lens when the image position of the object coincides with the image plane of the image sensor. The object is in focus in the plane (in-focus object plane) of the object that corresponds to the image plane, and the focal distance is indicated by the distance from the end of the objective lens to the in-focus object plane, for example. Specifically, the term "focal distance" used herein differs from the term "focal point" that is a point of convergence of parallel light incident on the lens, and the term "focal length" that is the distance from the lens to the focal point. The focus control process according to the first embodiment adjusts the focal distance by adjusting the position of the focus lens when implementing a zoom lens/focus lens drive operation, or adjusting the position of the zoom lens when implementing a zoom lens drive operation.

The above configuration makes it possible to switch the focus mode between the fixed focus mode and the AF mode based on the positional relationship between the reference point and the zoom lens 240. Note that the focus mode is switched between the fixed focus mode and the AF mode based on at least the positional relationship between the zoom lens 240 and the reference point. Specifically, the focus mode may be switched between the fixed focus mode and the AF mode based on the positional relationship between the zoom lens 240 and the reference point so that the focus mode is set to the fixed focus mode when the zoom lens 240 is positioned on the wide-angle side, and set to the AF mode when the zoom lens 240 is positioned on the telescopic side (third embodiment). The focus mode may be switched between the fixed focus mode and the AF mode taking account of additional conditions (e.g., AF start signal) in addition to the positional relationship between the zoom lens 240 and the reference point so that the focus mode is set to the fixed focus mode when the zoom lens 240 is positioned on the wide-angle side, and can be switched between the fixed focus mode and the AF mode (e.g., switched between the fixed focus mode and the AF mode based on the presence or absence of the AF start signal) when the zoom lens 240 is positioned on the telescopic side (first embodiment). This makes it possible to cause the focal distance control device, the endoscope system, and the like that can implement the AF operation to appropriately perform the AF operation instead of always performing the AF operation. In particular, a hollow tubular object may be observed using the endoscope system, as illustrated in FIG. 4A. In this case, the distance to the object differs to a large extent depending on the position of the object within the acquired image (e.g., the distance to the object is short in the peripheral area of the image, and is long in the center area of the image). Since only a limited area within the image is brought into focus when the AF operation is performed in such a state, the AF operation cannot achieve a sufficient effect, and may hinder observation by the user. Therefore, the AF operation is performed when the AF operation is effective (e.g., when the distance to the object does not differ to a large extent depending on the position of the object within the image (see FIG. 4B)).

The focus lens control section 330 may determine the position of the focus lens so that the in-focus object distance monotonously decreases when the position of the zoom lens 240 has moved from the wide-angle side to the telescopic side in a state in which the fixed focus mode is selected as the focus mode.

Note that the term "in-focus object distance" used herein refers to the distance from the imaging optical system to the object when the object image that is formed by light incident on the image sensor 280 through the imaging optical system is in focus. Even if the light does not converge at one point on the image sensor 280, it is considered that the object image is in focus when the size thereof is smaller than the permissible circle of confusion. Therefore, the in-focus object distance has a certain range. The in-focus object distance may be a value having such a range. Note that the in-focus object distance refers to the best object distance in a narrow sense. The term "best object distance" used herein refers to the distance from the imaging optical system to the object when light incident on the image sensor 280 through the imaging optical system converges at one point on the image sensor 280.

The above configuration makes it possible to implement the imaging optical system illustrated in FIG. 6A. The in-focus object distance (best object distance) decreases as the position of the zoom lens is moved from the wide-angle side to the telescopic side. Specifically, the depth-of-field range is set at a position closer to the imaging optical system (i.e., an object positioned close to the imaging optical system is brought into focus). In particular, it is considered that zoom observation is performed using the endoscope system or the like when the zoom lens 240 is moved to the telescopic side (i.e., the zoom magnification is increased). In this case, the end of the insertion section (imaging section 200) is normally moved closer to the object (observation target). Specifically, since it is considered that the distance between the imaging optical system and the object decreases as the position of the zoom lens 240 is moved to the telescopic side, it is easy to bring the object into focus by utilizing the optical system illustrated in FIG. 6A.

The optical system used in connection with the first embodiment is a zoom lens/focus lens drive optical system. The zoom lens/focus lens drive optical system is configured so that both the zoom lens and the focus lens can be driven. In this case, a configuration may be employed in which only the zoom magnification changes (i.e., the best object distance does not change) when the position of the zoom lens 240 is moved from the wide-angle side to the telescopic side (i.e., the configuration used for a digital still camera and the like). In such a case, the focus lens control section 330 moves the position of the focus lens 250 so that the best object distance decreases when the position of the zoom lens is moved to the telescopic side.

The focus lens control section 330 may select the fixed focus mode as the focus mode when the zoom lens 240 is positioned on the wide-angle side relative to the reference point, and switch the focus mode between the fixed focus mode and the AF mode when the zoom lens 240 is positioned on the telescopic side relative to the reference point, the fixed focus mode being a mode in which the focus lens 250 is set at a given position corresponding to the position of the zoom lens.

According to the above configuration, the focus mode is set to the fixed focus mode, and the AF operation is not performed when the zoom lens 240 is positioned on the wide-angle side relative to the reference point (i.e., when it is considered that a lesion area is searched (screening is performed) using the endoscope system or the like). It is considered that the distance to the object differs to a large extent corresponding to the position of the object within the image (see FIG. 4A) during screening or the like. Moreover, the observation area may change to a large extent when the end of the insertion section is moved or rotated when searching a lesion area. Therefore, the AF operation is not effective during screening or the like. When the zoom lens 240 is positioned on the telescopic side relative to the reference point, it is considered that zoom observation or the like is performed using the endoscope system. Therefore, the AF mode is allowed to be selected in addition to the fixed focus mode. Note that the focus mode may be switched between the fixed focus mode and the AF mode based on instructions issued by the user, for example. Specifically, the user may set the focus mode to the fixed focus mode that does not utilizes the AF operation, or set the focus mode to the AF mode. When the AF mode has been selected, the AF operation is performed, and the object can be easily brought into focus. Since a normal observation technique can also be used by allowing the user to select the fixed focus mode, it possible to enlarge the range of selection for the user.

The focus lens control section 330 may set the focus mode to the AF mode when the AF start signal has been input in a state in which the zoom lens 240 is positioned on the telescopic side relative to the reference point, and set the focus mode to the fixed focus mode when the AF start signal has not been input in a state in which the zoom lens 240 is positioned on the telescopic side relative to the reference point.

The above configuration makes it possible to set the focus mode based on whether or not the AF start signal has been input when the zoom lens 240 is positioned on the telescopic side relative to the reference point. The AF start signal is a signal that instructs the focus lens control section 330 to start the AF operation. For example, the AF start signal is input to the focus lens control section 330 when the AF button 620 of the operation section 600 has been pressed. It is possible to clearly reflect the user's intention by utilizing the AF button 620. Note that the configuration is not limited thereto. For example, the AF start signal may be output from the image processing section 340 to the focus lens control section 330 according to a determination based on image processing performed by the image processing section 340, or another method may be used. The above configuration makes it possible to set the focus mode taking account of the AF start signal in addition to the positional relationship between the zoom lens 240 and the reference point.

The focus lens control section 330 may set the focus mode to the fixed focus mode even when the AF start signal has been input when the zoom lens 240 is positioned on the wide-angle side relative to the reference point.

The above configuration makes it possible to set the focus mode to the fixed focus mode even when the AF start signal has been input when the zoom lens 240 is positioned on the wide-angle side. It is considered that screening or the like is performed using the endoscope system, and the AF operation is not effective when the zoom lens 240 is positioned on the wide-angle side relative to the reference point. When the focus mode is set to the AF mode in such a state, observation by the user may be hindered (e.g., only a narrow area of the image is brought into focus). Therefore, it is desirable to set the focus mode to the fixed focus mode even when the AF start signal has been input when the zoom lens 240 is positioned on the wide-angle side.

The focal distance control device may include the zoom lens control section 320 that controls the position of the zoom lens 240 (see FIG. 1). The zoom lens control section 320 may continuously control the position of the zoom lens 240.

The above configuration makes it possible to continuously control the position of the zoom lens. The position of the zoom lens may be continuously controlled using the zoom lever 610 illustrated in FIG. 7, for example. This makes it possible to finely set the position of the zoom lens 240.

The focus lens control section 330 may implement a single AF mode or a continuous AF mode when the AF mode has been selected as the focus mode.

The single AF mode refers to a mode in which the object is brought into focus only once. For example, the object is brought into focus in the single AF mode when the shutter release button of a digital still camera or the like has been pressed halfway. Since the object is brought into focus only once, the object becomes out of focus when distance to the object has changed due to the movement of the object or the like. The continuous AF mode refers to a mode in which the object is continuously brought into focus. When the object has moved in the continuous AF mode, the object is brought into focus again.

The above configuration makes it possible to use both the single AF mode and the continuous AF mode. Whether to use the single AF mode or the continuous AF mode may be determined by the system, or may be determined by the user using the operation section 600 or the like.

According to the first embodiment, the endoscope system includes the imaging optical system that includes the zoom lens 240 that adjusts the optical magnification, and the focus lens 250 that adjusts the focal distance, the image sensor 280 that generates an image that corresponds to the object image formed by the imaging optical system, and the focus lens control section 330 that controls the position of the focus lens 250, and sets the focus mode of the imaging optical system (see FIG. 1).

The above configuration makes it possible to implement an endoscope system that can switch the focus mode between the fixed focus mode and the AF mode based on the positional relationship between the reference point and the zoom lens 240. It is advantageous for the endoscope system to determine the position of the focus lens 250 in the fixed focus mode so that the in-focus object distance (best object distance) monotonously decreases when the position of the zoom lens has moved from the wide-angle side to the telescopic side, as described above. Specifically, since it is considered that a zoom operation is also performed by moving the end of the insertion section closer to the object during zoom observation in which the position of the zoom lens is moved to the telescopic side, the object can be more easily brought into focus as the in-focus object distance decreases.

The focus lens control section 330 included in the endoscope system may select the fixed focus mode as the focus mode when the zoom lens 240 is positioned on the wide-angle side relative to the reference point, and switch the focus mode between the fixed focus mode and the AF mode when the zoom lens 240 is positioned on the telescopic side relative to the reference point, the fixed focus mode being a mode in which the focus lens 250 is set at a given position corresponding to the position of the zoom lens.

The above configuration makes it possible to implement an endoscope system that selects the fixed focus mode when the zoom lens 240 is positioned on the wide-angle side, and can switch the focus mode between the fixed focus mode and the AF mode when the zoom lens 240 is positioned on the telescopic side.

2. Second Embodiment

An endoscope system according to a second embodiment of the invention is described below. FIG. 8 is a view illustrating an example of an operation section 600 according to the second embodiment. The operation section 600 according to the second embodiment is integrated with an imaging section 200, for example. The operation section 600 includes an AF button 620 and a zoom button 630. The remaining configuration is the same as described above in connection with the first embodiment.

The operation section 600 outputs the position information about the zoom lens to the zoom lens control section 320 when the zoom button 630 has been pressed, for example. More specifically, the operation section 600 sequentially outputs information corresponding to the position A, B, C, or D illustrated in FIG. 6A each time the zoom button 630 has been pressed, for example. The zoom lens control section 320 outputs the position information about the zoom lens output from the operation section 600 to the zoom lens driver section 260. The zoom lens driver section 260 drives the zoom lens based on the position information about the zoom lens output from the zoom lens control section 320. The zoom lens control section 320 also outputs the position information about the zoom lens to the focus lens control section 330. The operation section 600 alternately outputs the AF start/stop signal to the focus lens control section 330 each time the AF button 620 has been pressed, for example.

The focus lens control section 330 determines the observation mode in the same manner as described above in connection with the first embodiment based on the position information about the zoom lens output from the zoom lens control section 320, and the AF start/stop information output from the operation section 600, and controls the position of the focus lens. According to the above configuration, the observation mode determination section 331 selects the fixed focus mode, and the best object distance and the depth-of-field range change corresponding to the position A, B, C, or D (see FIG. 6A) when the user repeatedly presses the zoom button 630. This makes it possible for the user to bring the object into focus by pressing the zoom button 630 instead of operating the zoom lever 610 (see first embodiment).

Since the depth of field becomes shallow when the zoom lens is set to the position D, it is difficult for the user to bring the object into focus. In this case, the user starts the AF operation by pressing the AF button 620. The AF mode is then selected by the observation mode determination section 331, and the position of the focus lens is controlled corresponding to the distance to the object (see FIG. 6B). Therefore, the user can easily bring the object into focus.

In the second embodiment, it is assumed that the optical magnification is sufficient for zoom observation when the best object distance is minimized by moving the position of the focus lens in a state in which the zoom lens is set to the position D. If the optical magnification when the zoom lens is set to the position D is insufficient for zoom observation, the optical magnification may be increased by changing the position of the zoom lens within the range of A to E or A to F, for example.

When the position of the zoom lens is changed within the range of A to D, the position B may be omitted so that the zoom lens is sequentially set to the position A, the position C, and the position D when the user repeatedly presses the zoom button 630. Since the depth-of-field range is relatively deep when the zoom lens is set to the position A, B, or C, the user can easily bring the object into focus by adjusting the position of the imaging section 200 even when the depth-of-field range does not change continuously (e.g., the position B is omitted).

According to the second embodiment, the focal distance control device includes the zoom lens control section 320 that controls the position of the zoom lens 240. The zoom lens control section 320 discretely controls the position of the zoom lens 240.

The above configuration makes it possible to discretely control the position of the zoom lens. For example, a position among the positions A to F illustrated in FIGS. 6A and 6B is selected. According to the second embodiment, the range of selection of the position of the zoom lens is narrowed as compared with the first embodiment in which the position of the zoom lens is continuously controlled. However, since the user need not finely control the position of the zoom lens, the zoom lens position setting operation can be facilitated. Note that the position of the zoom lens may be discretely controlled using the zoom button 630 or the like.

The zoom lens control section 320 may select a first zoom lens position or a second zoom lens position as a discrete position of the zoom lens, the first zoom lens position being a position on the wide-angle side relative to the reference point, and the second zoom lens position being a position on the telescopic side relative to the reference point. The focus lens control section 330 may switch the focus mode between the fixed focus mode and the AF mode corresponding to whether the zoom lens 240 is set to the first zoom lens position or the second zoom lens position.

The above configuration makes it possible for the user to perform observation while switching the position of the zoom lens between two positions. The focus mode may be switched between the fixed focus mode and the AF mode so that the fixed focus mode is selected at the first zoom lens position on the wide-angle side, and the fixed focus mode or the AF mode can be selected at the second zoom lens position on the telescopic side. In this case, since the position of the zoom lens can be limited, the operation performed by the user can be facilitated. Specifically, since it suffices for the user to switch the mode between a wide-angle mode (first zoom lens position) that does not utilize the AF operation and a telescopic mode (second zoom lens position) that can utilize the AF operation, the burden imposed on the user can be reduced as compared with continuous zoom lens position control, and discrete zoom lens position control that can select a number of zoom lens positions.

3. Third Embodiment

An endoscope system according to a third embodiment of the invention is described below with reference to FIG. 10. An operation section 600 according to the third embodiment includes a zoom lever 610, and does not include an AF button 620, for example. Information output from the operation section 600 is output to a zoom lens control section 320, but is not output to a focus lens control section 330. The remaining configuration is the same as described above in connection with the first embodiment.

The details of the focus lens control section 330 according to the third embodiment are described below with reference to FIG. 3. The focus lens control section 330 (focus control section in a broad sense) includes an observation mode determination section 331, a focus lens position determination section 332, and an AF control section 333. The observation mode determination section 331 determines the observation mode based on the position information about the zoom lens output from the zoom lens control section 320. Specifically, the observation mode determination section 331 selects the fixed focus mode when the zoom lens is positioned on the WIDE side relative to the given position D, and outputs the position information about the zoom lens to the focus lens position determination section 332. The focus lens position determination section 332 determines the position of the focus lens based on the position information about the zoom lens, and outputs the position information about the focus lens to the focus lens driver section 270. The focus lens driver section 270 drives the focus lens based on the position information about the focus lens output from the focus lens position determination section 332. The position of the focus lens when the fixed focus mode is selected is determined in the same manner as described above in connection with the first embodiment.

The observation mode determination section 331 selects the AF mode when the zoom lens is positioned on the TELE side relative to the given position D, and outputs the AF start signal to the AF control section 333. The AF control section 333 starts the AF operation according to the AF start signal output from the observation mode determination section 331. In the third embodiment, the AF operation automatically starts when the zoom lens has been positioned on the TELE side relative to the given position D, and the depth of field has become shallow. According to the above configuration, since the user can start the AF operation by operating only the zoom lever 610 without using the AF button 620, the user can easily perform observation. The AF control section 333 may determine whether or not an in-focus state has occurred from the calculated contrast value, and stop the AF operation when it has been determined that the in-focus state has occurred. Alternatively, the AF control section 333 may drive the focus lens based on a known continuous AF technique so that the AF operation is continuously performed until the AF stop signal is output from the observation mode determination section 331. The observation mode determination section 331 may select the fixed focus mode when the zoom lens is positioned on the WIDE side relative to the given position D, and a continuous AF operation is performed, output the position information about the zoom lens to the focus lens position determination section 332, and output a continuous AF stop signal to the AF control section 333, for example. According to the above configuration, the user can stop the continuous AF operation even when the AF control section 333 performs the continuous AF operation by moving the zoom lever 610 toward the WIDE end.

According to the third embodiment, the focus lens control section 330 selects the fixed focus mode as the focus mode when the zoom lens 240 is positioned on the wide-angle side relative to the reference point, and selects the AF mode when the zoom lens 240 is positioned on the telescopic side relative to the reference point, the fixed focus mode being a mode in which the focus lens 250 is set at a given position corresponding to the position of the zoom lens.

The above configuration makes it possible to select the AF mode when the zoom lens is positioned on the telescopic side without using additional information such as the AF start signal, differing from the first embodiment. When the zoom lens is positioned on the telescopic side, the depth of field is very shallow since the zoom magnification is high, and the best object distance is short. Since it is difficult to manually bring the object in focus due to the motion of the object (e.g., movement due to pulsation when observing tissue using an endoscope system) or the motion of the optical system (e.g., shake), it is considered that the user selects the AF mode that implements the AF operation. According to the above configuration, since the AF mode can be selected without operating the AF button 620 (see FIG. 7) or the like, it is possible to provide a system that is highly convenient to the user.

The focus lens control section 330 may stop the AF mode, and set the focus mode to the fixed focus mode when the zoom lens 240 has been positioned on the wide-angle side relative to the reference point in a state in which the AF mode is selected as the focus mode.

The above configuration makes it possible to use a condition whereby the zoom lens 240 has been positioned on the wide-angle side relative to the reference point as the AF mode stop condition. In the single AF mode, it may be unnecessary to take account of the stop condition since the object is brought into focus only once. However, since the object is continuously brought into focus in the continuous AF mode, it is necessary to set an appropriate stop condition, and stop the focus operation when the stop condition has been satisfied.

The third embodiment also relates to the following endoscope system. The focus lens control section 330 included in the endoscope system selects the fixed focus mode as the focus mode when the zoom lens 240 is positioned on the wide-angle side relative to the reference point, and selects the AF mode when the zoom lens 240 is positioned on the telescopic side relative to the reference point, the fixed focus mode being a mode in which the focus lens 250 is set at a given position corresponding to the position of the zoom lens.

The above configuration makes it possible to implement an endoscope system that selects the fixed focus mode when the zoom lens 240 is positioned on the wide-angle side, and selects the AF mode when the zoom lens 240 is positioned on the telescopic side.

4. Fourth Embodiment

As described above, the user of an endoscope system may normally closely observe the object while moving the endoscope system closer to the object, and it may be difficult to obtain a stationary image during zoom observation due to the motion of tissue or the shake of the end of the scope. Therefore, an autofocus (AF) function has been required for the endoscope system.

For example, JP-A-8-106060 discloses an endoscope system having a configuration in which a focus driver section that drives the focus of an objective optical system is provided in an imaging section, and an AF operation is performed on the object.

In JP-A-8-106060, however, the AF operation is stopped or started using a switch provided to an operation section. Therefore, since the user must perform an AF stop/start operation in addition to a normal endoscope operation, the operation becomes complex.

JP-A-2002-253488 discloses an endoscope system that detects the distance to the object, performs an AF operation corresponding to the distance to the object, and includes a switch that enables or disables (ON/OFF) the AF operation on condition that the distance to the object is within a given range for a time equal to or more than a given time.

However, when the user has inserted the endoscopic scope in which the imaging section is disposed on its end into a living body, the user normally performs wide-field screening in order to find an attention area (e.g., lesion candidate). In this case, if the autofocus operation is continuously performed, the field of view increases and decreases within a short time, and observation is adversely affected. Moreover, the user cannot determine the in-focus distance if the distance to the in-focus object frequently changes. When the user has found an attention area during screening, the user moves the end of the scope closer to the attention area, and closely observes the attention area. In this case, it is desirable to perform the continuous autofocus operation to provide an image without shake so that the user can carefully observe the attention area.

According to several embodiments of the invention, the focus mode is automatically set corresponding to the observation state. More specifically, the focus mode is set to the continuous AF mode during zoom observation, and is not set to the continuous AF mode during wide-field observation.

According to the above configuration, since the distance to the in-focus object does not change during screening, the user can determine the in-focus distance. Moreover, observation is not adversely affected since a change in field of view due to the AF operation does not occur. Since the continuous AF operation is performed during zoom observation, it is possible to provide an image in which the observation target for the user is brought into focus.

A fourth embodiment and a sixth embodiment illustrate an endoscope system that implements a zoom lens drive operation and a phase detection AF operation, and a fifth embodiment illustrates an endoscope system that implements a zoom lens/focus lens drive operation and a contrast AF operation. Note that the combination of the lens drive method and the AF method is not limited thereto.

FIG. 11 illustrates a configuration example of an endoscope system according to the fourth embodiment that switches the mode between the continuous AF mode and the single AF mode. The endoscope system illustrated in FIG. 11 includes an imaging section 10 (insertion section), an A/D conversion section 20, a signal processing section 30 (image processing section), a focus control section 35, an output section 70 (display section), a control section 80, and an I/F section 90 (operation section and external interface section). The imaging section 10 includes a zoom lens 12 that adjusts the optical magnification, and an image sensor 14 that captures an image of the object. The focus control section 35 includes a phase difference calculation section 40 that calculates the phase difference, a driver section 50 that drives the zoom lens 12, and a switch section 60 that switches the mode.

The A/D conversion section 20 converts analog signals obtained by an imaging operation through the zoom lens 12 and the image sensor 14 into digital signals. The A/D conversion section 20 is connected to the signal processing section 30 and the phase difference calculation section 40. The signal processing section 30 is connected to the output section 70. The phase difference calculation section 40 is connected to the driver section 50. The driver section 50 is connected to a drive mechanism (not illustrated in FIG. 11) that moves the position of the zoom lens 12. The driver section 50 is bidirectionally connected to the switch section 60. The control section 80 that is implemented by a microcomputer or the like is bidirectionally connected to the A/D conversion section 20, the signal processing section 30, the phase difference calculation section 40, the driver section 50, the switch section 60, and the output section 70. The external I/F section 90 that includes a power switch and a variable setting interface is bidirectionally connected to the control section 80.

The operation of the endoscope system according to the fourth embodiment is described below. An image of reflected light from the object is formed on the image sensor 14 through the zoom lens 12 (i.e., an imaging lens group (not illustrated in FIG. 11) that includes the zoom lens 12). The image sensor 14 performs a photoelectric conversion process on the image, and outputs the resulting analog signals to the A/D conversion section 20. The A/D conversion section 20 converts the analog signals input from the image sensor 14 into digital signals, and outputs the digital signals to the signal processing section 30. The image sensor 14 includes a phase difference detection device for detecting the phase difference between two images corresponding to divided pupils. The details of the image sensor 14 that includes the phase difference detection device are described later. The A/D conversion section 20 converts analog signals acquired by the phase difference detection device into digital signals, and outputs the digital signals to the phase difference calculation section 40.

The phase difference calculation section 40 calculates the phase difference (phase difference information) based on the digital signals converted by the A/D conversion section 20 from the analog signals acquired by the phase difference detection device. The phase difference calculation section 40 determines the position of the zoom lens 12 at which the object is brought into focus (hereinafter appropriately referred to as "in-focus lens position") based on the calculated phase difference.

The driver section 50 stores information about the current position of the zoom lens 12. The driver section 50 sequentially moves the zoom lens 12 from the current position to the in-focus lens position based on information about the in-focus lens position sequentially determined by the phase difference calculation section 40 when the continuous AF mode (i.e., a mode in which the continuous AF operation (sequential AF operation) is performed) is enabled (ON). Specifically, when the continuous AF mode is enabled (ON), the position of the zoom lens 12 is moved each time the in-focus lens position has changed, and the object is always brought into focus.

The driver section 50 performs the single AF operation based on information about the in-focus lens position when the continuous AF mode is disabled (OFF) (i.e., when the single AF mode is enabled (ON)). Specifically, the zoom lens 12 is moved to the in-focus lens position once each time at given intervals instead of sequentially moving the zoom lens 12 each time the in-focus lens position has changed.

The switch section 60 enables/disables (ON/OFF) the continuous AF mode. Specifically, the switch section 60 switches the mode between the continuous AF mode and the single AF mode. More specifically, the switch section 60 acquires the information about the current position of the zoom lens 12 from the driver section 50. The switch section 60 disables the continuous AF mode when the current position of the zoom lens 12 is situated on the wide-angle side relative to a given position Dw (see FIG. 12). The switch section 60 enables the continuous AF mode when the current position of the zoom lens 12 is situated on the telescopic side relative to a given position Dt. Note that the position Dw and the position Dt may be either identical or different. The switch section 60 transmits information that indicates that the continuous AF mode is enabled or disabled (ON/OFF) to the driver section 50.

The signal processing section 30 performs image processing (e.g., grayscale transformation process) on the image (digital signals) output from the A/D conversion section 20. The output section 70 stores the image subjected to image processing by the signal processing section 30 in a recording medium (e.g., memory card), or outputs the image subjected to image processing by the signal processing section 30 to a display (not illustrated in FIG. 11).

A specific operation according to the fourth embodiment in the actual usage situation is described below. The user inserts the endoscopic scope in which the imaging section 10 is disposed on its end into a living body, and starts a diagnosis. The user initially performs wide-field screening in order to find an attention area (e.g., lesion candidate). When the user has started wide-field observation, the switch section 60 disables the continuous AF mode (initial setting).

Signals are acquired by the phase difference detection device included in the image sensor 14, and converted into digital signals by the A/D conversion section 20. The phase difference is calculated by the phase difference calculation section 40 based on the digital signals, and the in-focus lens position is sequentially determined based on the phase difference.

Since the continuous AF mode is disabled, the driver section 50 drives the zoom lens 12 once each time to the in-focus lens position determined by the phase difference calculation section 40 at given time intervals.

The switch section 60 acquires the information about the current position of the zoom lens 12 from the driver section 50, and determines whether or not to switch the mode. The switch section 60 does not enable the continuous AF mode when the current position of the zoom lens 12 is situated on the wide-angle side relative to the given position Dw.

When the user has found an attention area during screening, the user moves the end of the scope closer to the attention area, and closely observes the attention area. The driver section 50 that drives the zoom lens 12 once each time to the in-focus lens position at given time intervals then drives the zoom lens 12 to a position on the telescopic side relative to the given position Dt in order to perform zoom observation. The switch section 60 enables the continuous AF mode when it has been determined that the information about the current position of the zoom lens 12 acquired from the driver section 50 indicates that the current position of the zoom lens 12 is situated on the telescopic side relative to the given position Dt, and transmits information that indicates that the continuous AF mode is enabled to the driver section 50.

The phase difference calculation section 40 sequentially determines the in-focus lens position. When the continuous AF mode has been enabled, the driver section 50 sequentially drives the zoom lens 12 to the in-focus lens position determined by (transmitted from) the phase difference calculation section 40. Specifically, the driver section 50 performs the continuous AF operation.

When the user has finished checking the attention area, the user starts wide-field screening (observation) again. The driver section 50 that sequentially drives the zoom lens 12 to the in-focus lens position drives the zoom lens 12 to a position on the wide-angle side when the user has started wide-field observation. The switch section 60 disables the continuous AF mode when it has been determined that the information about the current position of the zoom lens 12 acquired from the driver section 50 indicates that the current position of the zoom lens 12 is situated on the wide-angle side relative to the given position Dw, and the driver section 50 performs the single AF operation.

The zoom lens 12 may be moved to a given fixed position Dz that corresponds to a deep depth of field (i.e., the position Dz in FIG. 12) when the continuous AF mode has been disabled. Since the position Dz is situated on the wide-angle side relative to the given position Dw, and corresponds to a deep depth of field, it is possible to easily achieve a state in which the object is brought into focus when the continuous AF mode has been disabled (i.e., when the continuous AF operation has been stopped).

According to the fourth embodiment, a focus control device includes the focus control section 35 that controls the focus of the imaging optical system that includes at least the zoom lens 12 that adjusts the optical magnification, and sets the focus mode of the imaging optical system, and an image acquisition section that acquires an image through the imaging optical system (see FIG. 11). As described above with reference to FIG. 12, the focus control section 35 sets the focus mode to the continuous AF mode when the zoom lens 12 is positioned on the wide-angle side relative to the reference point Dw that is positioned between the wide-angle end and the telescopic end, and disables the continuous AF mode when the zoom lens 12 is positioned on the telescopic side relative to the reference point Dt.

More specifically, the focus control section 35 sets the focus mode to the single AF mode when the zoom lens 12 is positioned on the telescopic side relative to the reference point Dt.

According to the above configuration, since the focus mode can be set to the continuous AF mode during zoom observation, it is possible to provide the user with a clear image in which the object is brought into focus even during high-magnification observation with a shallow depth of field. Since the focus mode can be set to the single AF operation during normal observation, the focus is maintained for a given time (i.e., does not change within a short time). Therefore, the user can easily determine the in-focus distance during screening or the like. Moreover, since the AF operation is performed at given time intervals, the user need not adjust the focus, and the burden imposed on the user can be reduced.

5. Fifth Embodiment

The fifth embodiment that implements a zoom lens/focus lens drive operation and a contrast AF operation is described below. FIG. 13 illustrates a configuration example of an endoscope system according to the fifth embodiment.

The endoscope system illustrated in FIG. 13 includes an imaging section 10, an A/D conversion section 20, a signal processing section 30, a focus control section 35, an output section 70, a control section 80, and an I/F section 90. The imaging section 10 includes a focus lens 11 that adjusts the focus, a zoom lens 12 that adjusts the optical magnification, and an image sensor 14. The focus control section 35 includes a contrast calculation section 42 that calculates the contrast value, an in-focus position determination section 44 that determines the in-focus lens position, a driver section 50 that drives the focus lens 11 and the zoom lens 12, and a switch section 60. The control section 80 includes a zoom magnification setting section 82.

Note that the elements identical to those described above in connection with the fourth embodiment are indicated by identical reference signs, and description thereof is appropriately omitted. The following description focuses on the configuration and the operation that differ from those described above in connection with the fourth embodiment.

The A/D conversion section 20 converts analog signals obtained by an imaging operation through the focus lens 11, the zoom lens 12, and the image sensor 14 into digital signals. The A/D conversion section 20 is connected to the signal processing section 30. The signal processing section 30 is connected to the contrast calculation section 42 and the output section 70. The contrast calculation section 42 is connected to the in-focus position determination section 44. The in-focus position determination section 44 is connected to the driver section 50. The driver section 50 is connected to a drive mechanism (not illustrated in FIG. 13) that moves the position of the focus lens 11, and a drive mechanism (not illustrated in FIG. 13) that moves the position of the zoom lens 12. The driver section 50 is bidirectionally connected to the switch section 60. The control section 80 that is implemented by a microcomputer or the like is bidirectionally connected to the A/D conversion section 20, the signal processing section 30, the contrast calculation section 42, the in-focus position determination section 44, the driver section 50, the switch section 60, and the output section 70. The I/F section 90 that includes a power switch and a variable setting interface is bidirectionally connected to the control section 80. The I/F section 90 may further include a lever that allows the user to manually move the position of the zoom lens, for example.

The operation of the endoscope system according to the fifth embodiment is described below. An image of reflected light from the object is formed on the image sensor 14 through the focus lens 11 and the zoom lens 12 (i.e., an imaging lens group (not illustrated in FIG. 13) that includes the focus lens 11 and zoom lens 12). The image subjected to A/D conversion by the A/D conversion section 20 is subjected to image processing by the signal processing section 30, and the resulting image is output to the contrast calculation section 42.

The driver section 50 moves the focus lens 11 to a plurality of positions (at least three or more positions) along the optical axis (wobbling), and the signal processing section 30 acquires the image at each position. The contrast calculation section 42 calculates the contrast value corresponding to each position. Specifically, the contrast calculation section 42 performs a high-pass filter process or a band-pass filter process on the image output from the signal processing section 30, and integrates the processing results within the image to calculate the contrast value.

The in-focus position determination section 44 determines the position (in-focus lens position) of the focus lens 11 at which the object is brought into focus based on a plurality of contrast values output from the contrast calculation section 42, and the position of the focus lens 11 corresponding to each contrast value. Specifically, the in-focus position determination section 44 calculates the position at which the contrast value becomes a peak (maximum) from a plurality of contrast values acquired corresponding to a plurality of lens positions, and determines the calculated position to be the in-focus lens position.

Note that the contrast AF method is not limited to the above hill-climbing contrast AF method. Another contrast AF method may also be employed. For example when the focus lens 11 is moved to two positions, and it has been determined that the contrast value at the current lens position has become smaller than a given value, the focus lens 11 may be moved to the other lens position.

The driver section 50 stores information about the current position of the zoom lens 12 and the current position of the focus lens 11. The switch section 60 enables or disables the continuous AF mode based on the information about the current position of the zoom lens 12 and the current position of the focus lens 11, and the driver section 50 performs the contrast AF operation or the single AF operation based on the information that indicates that the continuous AF mode is enabled or disabled. The switch operation is the same as that described above in connection with the fourth embodiment.

The driver section 50 includes a focus lens control section 52 that moves the position of the focus lens 11, and a zoom lens control section 54 that moves the position of the zoom lens 12. The focus lens control section 52 drives the focus lens 11 during the AF operation. The zoom lens control section 54 moves the zoom lens 12 to the position that corresponds to the optical magnification set by the zoom magnification setting section 82 included in the control section 80. Note that the optical magnification is set by the zoom magnification setting section 82 when the user has operated an operation section (e.g., zoom lever 610 illustrated in FIG. 7) included in the I/F section 90.

A specific operation according to the fifth embodiment in the actual usage situation differs from that according to the fourth embodiment in that the AF operation is a contrast AF operation, and the zoom lens/focus lens drive operation is performed.

In the fifth embodiment, the switch section 60 disables the continuous AF mode when it has been determined that the position of the focus lens 11 is situated on the wide-angle side relative to the given position Dw during screening. When the continuous AF mode is disabled, the focus control section 35 performs the contrast AF operation once at given time intervals. Specifically, the focus control section 35 performs the operation that determines the in-focus lens position by wobbling, and moves the focus lens 11 to the in-focus lens position once at given time intervals.

The switch section 60 enables the continuous AF mode when it has been determined that the position of the focus lens 11 is situated on the telescopic side relative to the given position Dt during zoom observation. When the continuous AF mode is enabled, the focus control section 35 sequentially performs the contrast AF operation. Specifically, the focus control section 35 sequentially determines the in-focus lens position by wobbling, and sequentially moves the focus lens 11 to the in-focus lens position.

According to the fifth embodiment, the continuous AF operation can be performed during zoom observation, and the single AF operation can be performed during normal observation when utilizing the contrast AF operation and the zoom lens/focus lens drive operation, and a clear image can be provided to the user.

6. Sixth Embodiment

The sixth embodiment that implements the fixed focus mode when the continuous AF mode is disabled is described below. FIG. 14 illustrates a configuration example of an endoscope system according to the sixth embodiment.

The endoscope system illustrated in FIG. 14 includes an imaging section 10, an A/D conversion section 20, a signal processing section 30, a focus control section 35, an output section 70, a control section 80, and an I/F section 90. The imaging section 10 includes a zoom lens 12 and an image sensor 14. The focus control section 35 includes a phase difference calculation section 40, a driver section 50, and a switch section 60. The control section 80 includes a zoom magnification setting section 82.

Note that the elements identical to those described above in connection with the fourth embodiment are indicated by identical reference signs, and description thereof is appropriately omitted. The following description focuses on the configuration and the operation that differ from those described above in connection with the fourth embodiment.

The phase difference calculation section 40 is connected to the switch section 60. The connection relationship between the remaining elements is the same as those described above in connection with the fourth embodiment.

The phase difference calculation section 40 calculates the phase difference based on the signals output from the phase difference detection device included in the image sensor 14, and calculates the position (in-focus lens position) of the zoom lens 12 at which the object is brought into focus based on the phase difference.

The switch section 60 acquires the information about the current position of the zoom lens 12 from the driver section 50 when the continuous AF mode is enabled, and determines whether or not to disable the continuous AF mode based on the information about the current position of the zoom lens 12. The switch section 60 acquires the in-focus lens position from the phase difference calculation section 40 when the continuous AF mode is disabled, and determines whether or not to enable the continuous AF mode based on the in-focus lens position. When the continuous AF mode is disabled, the zoom lens 12 is not moved as long as the optical magnification is not changed. However, whether the lens position at which the object is brought into focus is situated on the wide-angle side or the telescopic side can be determined based on the in-focus lens position.

Note that the switch section 60 may determine whether or not to disable the continuous AF mode based on the information about the in-focus lens position output from the phase difference calculation section 40 when the continuous AF mode is enabled. The switch section 60 may acquire the information about the current position of the zoom lens 12 that is set corresponding to the optical magnification from the driver section 50 when the continuous AF mode is disabled, and determine whether or not to enable the continuous AF mode based on the information about the current position of the zoom lens 12. For example, it is considered that it is not appropriate to perform the wobbling operation in the fixed focus mode when using the contrast AF operation. Therefore, whether or not to enable the continuous AF mode may be determined based on the current position of the zoom lens 12.

The driver section 50 sets the zoom lens 12 to the position that corresponds to the optical magnification set by the zoom magnification setting section 82 (or a given fixed position) when the continuous AF mode has been disabled (i.e., when the focus mode has been set to the fixed focus mode), and does not perform the AF operation. Note that the optical magnification is set by the zoom magnification setting section 82 when the user has operated an operation section (e.g., zoom lever 610 illustrated in FIG. 7) included in the I/F section 90. The operations of the remaining elements are the same as those described above in connection with the fourth embodiment.

A specific operation according to the sixth embodiment in the actual usage situation is described below. The user inserts the endoscopic scope in which the imaging section 10 is disposed on its end into a living body, and starts a diagnosis. The user initially performs wide-field screening in order to find an attention area (e.g., lesion candidate). When the user has started wide-field observation, the switch section 60 disables the continuous AF mode (initial setting).

Signals are acquired by the phase difference detection device included in the image sensor 14, and converted into digital signals by the A/D conversion section 20. The phase difference is calculated by the phase difference calculation section 40 based on the digital signals, and the in-focus lens position is sequentially determined based on the phase difference.

The switch section 60 acquires the information about the in-focus lens position from the phase difference calculation section 40, and determines whether or not to switch the mode. The switch section 60 disables (or does not enable) the continuous AF mode when the in-focus lens position is situated on the wide-angle side relative to the given position Dw (see FIG. 12). Specifically, the mode is set to the fixed focus mode during screening, and the zoom lens 12 is set to the fixed position corresponding to the optical magnification.

When the user has found an attention area during screening, the user moves the end of the scope closer to the attention area, and closely observes the attention area. The switch section 60 enables the continuous AF mode when it has been determined that the in-focus lens position acquired from the phase difference calculation section 40 (or the current position of the zoom lens 12 acquired from the driver section 50 when using the current position of the zoom lens 12 corresponding to the optical magnification) is situated on the telescopic side relative to the given position Dt, and transmits information that indicates that the continuous AF mode is enabled to the driver section 50.

When the continuous AF mode has been enabled, the driver section 50 sequentially drives the zoom lens 12 to the in-focus lens position determined by (transmitted from) the phase difference calculation section 40. Specifically, the driver section 50 performs the continuous AF operation.

When the user has finished checking the attention area, the user starts wide-field screening (observation) again. The driver section 50 that sequentially drives the zoom lens 12 to the in-focus lens position drives the zoom lens 12 to a position on the wide-angle side when the user has started wide-field observation. The switch section 60 disables the continuous AF mode when it has been determined that the current position of the zoom lens 12 acquired from the driver section 50 (or the in-focus lens position acquired from the phase difference calculation section 40) is situated on the wide-angle side relative to the given position Dw, and the driver section 50 stops the AF operation.

The zoom lens 12 may be moved to a given fixed position Dz that corresponds to a deep depth of field (i.e., the position Dz in FIG. 12) when the continuous AF mode has been disabled. Since the position Dz is situated on the wide-angle side relative to the given position Dw, and corresponds to a deep depth of field, it is possible to easily achieve a state in which the object is brought into focus when the continuous AF mode has been disabled (i.e., when the continuous AF operation has been stopped).

According to the sixth embodiment, since the focus mode is set to the continuous AF mode during zoom observation, it is possible to provide the user with a clear image in which the object is brought into focus even during high-magnification observation with a shallow depth of field. Since the focus mode is set to the fixed focus mode during normal observation, the focus is not changed as long as the user does not perform a focus change operation. Therefore, the user can easily determine the in-focus distance during screening or the like.

According to the sixth embodiment, a focus control device includes the focus control section that controls the focus of the imaging optical system that includes at least the zoom lens that adjusts the optical magnification, and sets the focus mode of the imaging optical system, and an image acquisition section that acquires an image through the imaging optical system. The focus mode includes the fixed focus mode and the AF (autofocus) mode. The focus control section switches the focus mode between the fixed focus mode and the AF mode corresponding to whether the zoom lens is positioned on the wide-angle side or the telescopic side relative to a reference point that is situated between the wide-angle end and the telescopic end.

Note that the focus control section corresponds to the focus lens control section 330 illustrated in FIG. 1 (first and second embodiments), or the focus lens control section 330 illustrated in FIG. 10 (third embodiment), or the focus control section 35 illustrated in FIG. 14 (sixth embodiment), for example. The focus may be controlled by the zoom lens/focus lens drive operation or the zoom lens drive operation, as described above with reference to FIG. 9 and the like. The single AF operation or the continuous AF operation may be performed in the AF mode, as described above in connection with the first embodiment and the like.

The position of the zoom lens refers to a position to which the zoom lens is actually set in the imaging optical system, or a position calculated to be a position at which the object is brought into focus (in-focus lens position) when implementing the zoom lens drive operation that brings the object into focus by moving the zoom lens. For example, the user operates the zoom lever 610 illustrated in FIG. 7, the zoom lens control section 320 illustrated in FIG. 1 moves the zoom lens 240 based on information about the operation performed by the user, and the focus lens control section 330 determines whether or not to switch the mode based on the position of the zoom lens 240, as described above in connection with the first embodiment and the like. Alternatively, the phase difference calculation section 40 calculates the in-focus lens position based on the phase difference in the fixed focus mode, and the switch section 60 determines whether or not to enable the continuous AF mode based on the in-focus lens position.

The above configuration makes it possible to switch the focus mode between the fixed focus mode and the AF mode based on at least the positional relationship between the reference point and the zoom lens. For example, the focus mode may be set to the fixed focus mode when the zoom lens is positioned on the wide-angle side, and set to the AF mode when the zoom lens is positioned on the telescopic side, as described above in connection with the third embodiment and the sixth embodiment. The focus mode may be set to the fixed focus mode when the zoom lens is positioned on the wide-angle side, and the focus mode may be switched between the fixed focus mode and the AF mode taking account of an additional condition (e.g., AF start signal) when the zoom lens is positioned on the telescopic side, as described above in connection with the first embodiment. This makes it possible to cause the AF operation to be appropriately performed instead of being always performed. In particular, it is possible to cause the endoscope system not to perform the AF operation when observing a hollow tubular object for which the AF operation is not effective (see FIG. 4A), and to perform the AF operation when the AF operation is effective (see FIG. 4B), as described above in connection with the first embodiment.

The focus control section may set the in-focus object distance to a given distance that corresponds to the position of the zoom lens in the fixed focus mode.

For example, the position of the zoom lens is linked to the in-focus object distance so that the in-focus object distance decreases as the zoom lens moves from the position A at the wide-angle end to the position F at the telescopic end (see FIG. 6A). When implementing the zoom lens/focus lens drive operation, when the position of the zoom lens has been set, the focus lens is moved corresponding to the position of the zoom lens to implement a given in-focus object distance. When implementing the zoom lens drive operation, since the in-focus object distance is adjusted by moving the zoom lens, a given in-focus object distance corresponding to the position of the zoom lens is set when the position of the zoom lens is moved.

The focus control section 35 may perform the AF control process based on the phase difference in the AF mode, as described above with reference to FIG. 14 (sixth embodiment) and the like. Specifically, the image acquisition section may further include the phase difference detection device for detecting the phase difference. The focus control section 35 may include the phase difference calculation section 40 that calculates the phase difference based on the signals output from the phase difference detection device. The focus control section 35 brings the object image into focus based on the calculated phase difference.

In the sixth embodiment, the phase difference detection device is included in the image sensor 14, as described above with reference to FIG. 13. The phase difference calculation section 40 calculates the in-focus lens position based on the phase difference, and the driver section 50 moves the zoom lens 12 to the in-focus lens position to control the focus.

The above configuration makes it possible to implement the phase detection AF operation in the AF mode. Since the in-focus lens position can be calculated by merely detecting the phase difference when using the phase detection AF operation, a high-speed AF operation can be normally implemented as compared with the case of using the contrast AF operation that moves the lens.

The focus control section 35 may set the zoom lens 12 to the given position Dz on the wide-angle side when stopping the AF mode, as described above with reference to FIG. 12 and the like.

According to the above configuration, a state in which the depth of field is deep can be implemented when stopping the AF mode. Specifically, since the focus mode is set to the fixed focus mode, and the AF operation is not performed when the AF mode has been stopped, the object may easily become out of focus if the depth of field is shallow. Such a situation is inconvenient to the user. Since the depth of field becomes deep by setting the zoom lens 12 to the given position Dz on the wide-angle side, it is possible to improve convenience to the user.

7. Phase Detection AF

The image sensor 14 that includes the phase difference detection device, and the phase detection AF method that utilizes the image sensor 14 are described below. Note that the phase detection AF method is not limited to the method described below. For example, various other phase detection AF methods (e.g., a method that implements pupil division using a spectacle lens) may also be employed.

FIG. 15 illustrates a configuration example of an image sensor that includes a phase difference detection device. The image sensor illustrated in FIG. 15 includes normal pixels R, G, and B having a Bayer color filter array, and phase sensors S1 and S2 (pixels S1 and S2) (phase difference detection devices).

The pixels S1 and S2 (phase sensors S1 and S2) correspond to the functional pixels S1 and S2 disclosed at paragraphs [0074] to [0083] of JP-A-2000-156823, for example. Each of the pixels S1 and S2 (phase sensors S1 and S2) has an opening that is biased from the center of the pixel in the lateral direction. The above configuration achieves an effect similar to that achieved when dividing the pupil of the imaging optical system in the lateral direction. Therefore, image signals from a plurality of phase sensors S1 and S2 arranged in the horizontal direction in FIG. 15 are considered to be the phase signals of a light beam that has passed through each pupil. For example, when the position of the object image formed by the imaging optical system coincides with the image plane of the image sensor (i.e., the object is in focus), the phase signals output from the phase sensors S1 coincide with the phase signals output from the phase sensors S2. When the position of the object image formed by the imaging optical system is situated in front of (or behind) the image plane of the image sensor (i.e., the object is out of focus), a phase difference occurs between the phase signals output from the phase sensors S1 and the phase signals output from the phase sensors S2. Note that only a pair of phase sensors S1 and S2 may be provided at the center of the imaging section, or a plurality of pairs of phase sensors S1 and S2 may be provided at arbitrary positions of the imaging section, for example.

The phase difference calculation section 40 calculates the moving amount of the movable lens as described below (see FIG. 16). Note that the movable lens is the zoom lens 12 when implementing the zoom lens drive operation, or the focus lens 11 when implementing the zoom lens/focus lens drive operation.

FIG. 16 is a view illustrating light beams that pass through divided pupils when the image position is situated behind the image plane. The light beam 1 is a light beam that has passed through the pupil corresponding to each phase sensor S 1, and the light beam 2 is a light beam that has passed through the pupil corresponding to each phase sensor S2. Since the image position is situated at a position differing from the image plane (i.e., a position behind the image plane), a phase difference S occurs between the phase signals output from the phase sensors S1 and the phase signals output from the phase sensors S2. Note that S is a positive or negative vector. The direction indicated by the arrow in FIG. 16 is the positive direction. The phase difference S may be calculated using a known phase detection AF technique. The distance between the image plane and the exit pupil is referred to as F, the distance between the centers of gravity of the divided pupils is referred to as G, and the defocus amount is referred to as d. Note that d is a positive or negative vector. The direction indicated by the arrow in FIG. 16 is the positive direction. In this case, the following expression (1) is satisfied, and the defocus amount d can be calculated using the following expression (2) obtained by transforming the expression (1). Note that the above description is similarly applied to the case where the image position is situated in front of the image plane. The defocus amount d may also be calculated by the method disclosed at paragraphs [0108] to [0110] of JP-A-2000-156823, for example.

$$G/(F+d) = S/d \quad (1)$$

$$d = F \cdot S/(G-S) \quad (2)$$

The phase difference calculation section 40 calculates the moving amount of the movable lens necessary for implementing an in-focus state from the defocus amount d calculated using the expression (2) for the phase signals sequentially output from the phase sensors S1 and S2 in the same cycle as the image signals, for example, and sequentially outputs the calculated moving amount to the driver section 50. Alternatively, the phase difference calculation section 40 may calculate the in-focus lens position from the moving amount of the movable lens and information about the current position of the movable lens, and sequentially output information about the calculated in-focus lens position to the driver section 50 (or the switch section 60 illustrated in FIG. 14). For example, the ratio R of the moving amount of the movable lens to the moving amount of the image position may be calculated in advance by the following expression (3) using the design data of the imaging optical system, and the moving amount D may be calculated by the following expression (4).

$$R = \text{moving amount of movable lens/moving amount of image position} \quad (3)$$

$$D = R \cdot d \quad (4)$$

For example, when the ratio R of the moving amount of the movable lens to the moving amount of the image position changes depending on the position x of the movable lens, the position xn (n is a natural number) of the movable lens and the ratio Rn may be stored in advance as a look-up table (LUT) (see FIG. 17), and the ratio Rn corresponding to the position xn of the movable lens at a timing at which the phase signals have been output from the phase sensors S1 and S2 may be used as the ratio R in the expression (4) to calculate the moving amount D.

When the distance F between the image plane and the exit pupil and the distance G between the centers of gravity of the pupils (see FIG. 16) also change depending on the position x of the movable lens, the distance Fn and the distance Gn corresponding to the position xn of the movable lens are also stored in the LUT (see FIG. 18). The distance Fn and the distance Gn corresponding to the position xn of the movable lens at a timing at which the phase signals have been output from the phase sensors S1 and S2 are used as the distance F and the distance G in the expression (2) to calculate the defocus amount dn. The calculated defocus amount dn and the ratio Rn corresponding to the position xn of the movable lens are used as the defocus amount d and the ratio R in the expression (4) to calculate the moving amount D. Note that it is unnecessary to take account of the parameter illustrated in FIG. 18 of which the change depending on the position of the movable lens is negligibly small. Another parameter that may be used to calculate the moving amount and changes to a large extent depending on the position of the movable lens may be added to the LUT.

The phase difference calculation section 40 may calculate and output the moving amount corresponding to all of the phase signals sequentially output from the phase sensors S1 and S2, or may sample the phase signals in an arbitrary cycle, and calculate and output the moving amount, for example. In the latter case, the moving amount is output from the phase difference calculation section 40 in a cycle longer than the image signal output cycle.

The focus control device and the like according to the embodiments of the invention may include a processor and a memory. The processor may be a central processing unit (CPU), for example. Note that the processor is not limited to a CPU. Various types of processors such as a graphics processing unit (GPU) and a digital signal processor (DSP) may also be used. The processor may be a hardware circuit such as an application specific integrated circuit (ASIC). The memory stores a computer-readable instruction. Each section of the focus control device and the like according to the embodiments of the invention is implemented by causing the processor to execute the instruction. The memory may be a semiconductor memory (e.g., SRAM or DRAM), a register, a hard disk, or the like. The instruction may be an instruction included in an instruction set of a program, or may be an instruction that causes a hardware circuit of the processor to operate.

The embodiments according to the invention and the modifications thereof have been described above. Note that the invention is not limited to the above embodiments and the modifications thereof. Various modifications and variations may be made of the above embodiments and the modifications thereof without departing from the scope of the invention. A plurality of elements described in connection with the above embodiments and the modifications thereof may be appropriately combined to implement various configurations. For example, some of the elements described in connection with the above embodiments and the modifications thereof may be omitted. The elements described in connection with different embodiments and/or modifications may be appropriately combined. Specifically, various modifications and applications are possible without materially departing from the novel teachings and advantages of the invention.

What is claimed is:

1. A focus control device comprising:
a memory having instructions stored therein; and
a processor which executes the instructions stored in the memory to:
control a focus of an imaging optical system, and set a focus mode of the imaging optical system, the imaging optical system including at least a zoom lens that adjusts an optical magnification, wherein the zoom lens is movable by a motor between a wide-angle side and a telescopic side relative to a reference point that is situated between a wide-angle end and a telescopic end; and
acquire, with an image sensor, an image through the imaging optical system,
wherein:
the focus mode includes a fixed focus mode and an autofocus (AF) mode,
the processor switches the focus mode between the fixed focus mode and the AF mode in correspondence with whether the zoom lens is positioned by the motor on the wide-angle side or the telescopic side relative to the reference point, and
the processor controls the focus so that an in-focus object distance monotonously decreases when a position of the zoom lens has moved from the wide-angle side toward the telescopic side in a state in which the fixed focus mode is selected as the focus mode.

2. The focus control device as defined in claim 1, wherein the processor selects the fixed focus mode as the focus mode when the zoom lens is positioned on the wide-angle side relative to the reference point, and switches the focus mode between the fixed focus mode and the AF mode when the zoom lens is positioned on the telescopic side relative to the reference point, the fixed focus mode being a mode in which the in-focus object distance is set to a given distance that corresponds to the position of the zoom lens.

3. The focus control device as defined in claim 1, wherein the processor selects the fixed focus mode as the focus mode when the zoom lens is positioned on the wide-angle side relative to the reference point, and selects the AF mode as the focus mode when the zoom lens is positioned on the telescopic side relative to the reference point, the fixed focus mode being a mode in which the in-focus object distance is set to a given distance that corresponds to the position of the zoom lens.

4. The focus control device as defined in claim 2, wherein the processor sets the focus mode to the AF mode when an AF start signal has been input in a state in which the zoom lens is positioned on the telescopic side relative to the reference point, and sets the focus mode to the fixed focus mode when the AF start signal has not been input in a state in which the zoom lens is positioned on the telescopic side relative to the reference point.

5. The focus control device as defined in claim 4, wherein the processor sets the focus mode to the fixed focus mode even when the AF start signal has been input when the zoom lens is positioned on the wide-angle side relative to the reference point.

6. The focus control device as defined in claim 3, wherein the processor stops the AF mode, and sets the focus mode to the fixed focus mode when the zoom lens has been positioned on the wide-angle side relative to the reference point in a state in which the AF mode is selected as the focus mode.

7. The focus control device as defined in claim 2, wherein the processor implements a single AF mode when the AF mode has been selected as the focus mode.

8. The focus control device as defined in claim 3, wherein the processor implements a single AF mode when the AF mode has been selected as the focus mode.

9. The focus control device as defined in claim 2, wherein the processor implements a continuous AF mode when the AF mode has been selected as the focus mode.

10. The focus control device as defined in claim 3, wherein the processor implements a continuous AF mode when the AF mode has been selected as the focus mode.

11. The focus control device as defined in claim 1, wherein the processor performs an AF control process based on a phase difference in the AF mode.

12. The focus control device as defined in claim 11, further comprising a phase difference detection device for detecting the phase difference,
wherein the processor is further configured to calculate the phase difference based on a signal output from the phase difference detection device, and
the processor brings an object image into focus based on the calculated phase difference.

13. The focus control device as defined in claim 1, wherein the processor sets the zoom lens to a given position on the wide-angle side when stopping the AF mode.

14. The focus control device as defined in claim 1, wherein the imaging optical system further includes a focus lens, and
the processor controls the focus by adjusting a position of the focus lens using a motor.

15. The focus control device as defined in claim 14, wherein the processor sets the focus lens to a given position that corresponds to a position of the zoom lens in the fixed focus mode.

16. The focus control device as defined in claim 14, wherein the processor controls a position of the zoom lens using the motor, and the processor continuously controls the position of the zoom lens.

17. The focus control device as defined in claim 14, wherein the processor controls a position of the zoom lens using the motor, and the processor discretely controls the position of the zoom lens.

18. The focus control device as defined in claim 17, wherein the processor selects a first zoom lens position or a second zoom lens position as a discrete position of the zoom lens, the first zoom lens position being a position on the wide-angle side relative to the reference point, and the second zoom lens position being a position on the telescopic side relative to the reference point, and the processor switches the focus mode between the fixed focus mode and the AF mode corresponding to whether the zoom lens is set to the first zoom lens position or the second zoom lens position.

19. The focus control device as defined in claim 1, wherein the processor controls the focus by adjusting a position of the zoom lens using the motor.

20. The focus control device as defined in claim 19, wherein the processor sets the optical magnification, and sets the position of the zoom lens to a position that corresponds to the optical magnification in the fixed focus mode.

21. The focus control device as defined in claim 14, wherein the processor fixes a position of the focus lens at a given reference position when the fixed focus mode has been selected as the focus mode.

22. An endoscope system comprising:
an imaging optical system that includes at least a zoom lens that adjusts an optical magnification, the zoom lens being movable by a motor;
an image sensor that generates an image that corresponds to an object image formed by the imaging optical system; and
a processor that executes instructions stored in a memory to control a focus of the imaging optical system, and set a focus mode of the imaging optical system,
wherein:
the focus mode includes a fixed focus mode and an autofocus (AF) mode, and
the processor switches the focus mode between the fixed focus mode and the AF mode in correspondence with whether the zoom lens is positioned by the motor on a wide-angle side or a telescopic side relative to a reference point that is situated between a wide-angle end and a telescopic end.

23. The endoscope system as defined in claim 22, the processor selects the fixed focus mode as the focus mode when the zoom lens is positioned on the wide-angle side relative to the reference point, and switches the focus mode between the fixed focus mode and the AF mode when the zoom lens is positioned on the telescopic side relative to the reference point, the fixed focus mode being a mode in which an in-focus object distance is set to a given distance that corresponds to a position of the zoom lens.

24. The endoscope system as defined in claim 22, wherein the processor selects the fixed focus mode as the focus mode when the zoom lens is positioned on the wide-angle side relative to the reference point, and selects the AF mode as the focus mode when the zoom lens is positioned on the telescopic side relative to the reference point, the fixed focus mode being a mode in which the in-focus object distance is set to a given distance that corresponds to a position of the zoom lens.

25. A focus control method that controls a focus of an imaging optical system that includes at least a zoom lens that adjusts an optical magnification and that is movable by a motor, a focus mode of the imaging optical system including a fixed focus mode and an autofocus (AF) mode, the method comprising:
switching the focus mode between the fixed focus mode and the AF mode in correspondence with whether the zoom lens is positioned by the motor on a wide-angle side or a telescopic side relative to a reference point that is situated between a wide-angle end and a telescopic end; and
controlling the focus of the imaging optical system based on the focus mode that has been set to the fixed focus mode or the AF mode.

* * * * *